(12) United States Patent
Tabart et al.

(10) Patent No.: US 7,947,706 B2
(45) Date of Patent: May 24, 2011

(54) SUBSTITUTED PYRROLOPYRIDINES, COMPOSITIONS CONTAINING THEM, MANUFACTURING PROCESS THEREFOR AND USE THEREOF

(75) Inventors: Michel Tabart, La Norville (FR); Eric Bacque, Gif sur Yvette (FR); Frank Halley, Chaville (FR); Baptiste Ronan, Clamart (FR); Pascal Desmazeau, Tigery (FR); Fabrice Viviani, Avenheim (FR); Catherine Souaille, Choisy le Roi (FR)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 651 days.

(21) Appl. No.: 11/870,640

(22) Filed: Oct. 11, 2007

(65) Prior Publication Data
US 2008/0139606 A1 Jun. 12, 2008

Related U.S. Application Data

(63) Continuation of application No. PCT/FR2006/000925, filed on Apr. 26, 2006.

(30) Foreign Application Priority Data

Apr. 26, 2005 (FR) ..................................... 05 04173

(51) Int. Cl.
*A61K 31/437* (2006.01)
*C07D 471/04* (2006.01)
*A61P 35/00* (2006.01)

(52) U.S. Cl. ........................................ 514/300; 546/113
(58) Field of Classification Search .................. 546/113; 514/300
See application file for complete search history.

(56) References Cited

U.S. PATENT DOCUMENTS

| 6,897,207 | B2 | 5/2005 | Cox et al. |
| 7,566,736 | B2 | 7/2009 | Halley et al. |
| 2005/0267304 | A1 | 12/2005 | Cox et al. |

FOREIGN PATENT DOCUMENTS

| WO | WO 01/98299 A1 | 12/2001 |
| WO | WO 03/000688 A1 | 1/2003 |
| WO | WO 03/028724 A1 | 4/2003 |
| WO | WO 03/082868 A1 | 10/2003 |

OTHER PUBLICATIONS van Riggelen Jan et al., Nature cell biology, (Jan. 2010) vol. 12, No. 1, pp. 7-9.*
Curtis et al., Bioorganic & Medicinal Chemistry Letters (1999), 9(4), 585-588.*
Cammarei et al., Cancer Research, 70(11), 2010, pp. 4655-4665.*
Oke et al., Cancer Research, vol. 69:(10), 2009, pp. 4150-4158.*
Sood et al., The journal of clinical investigation, vol. 120(5), 2010, pp. 1515-1523.*
Luo et al., Cancer Letters, vol. 289, 2010, pp. 127-139.*
Lin et al., J. Clin. Invest., vol. 100(8), 1997, pp. 2072-2078.*
Jean-Philippe Dales et al., International Journal of Oncology, vol. 22(2), 2003, pp. 391-397.*
Severine Meunier-Carpentier et al., International Journal of Oncology, vol. 26(4), 2005, pp. 977-984.*
U.S. Appl. No. 11/832,206, filed Aug. 1, 2007, Ronan et al.
U.S. Appl. No. 11/832,208, filed Aug. 1, 2007, Ronan et al.
U.S. Appl. No. 11/757613, Office Action dated Jan. 16, 2009.
Asahara et al, Tie2 Receptor Ligands, Angiopoietin-1 and Angiopoietin-2, Modulate VEGF-Induced Postnatal Neovascularization, Circ. Res., 1998 (83) pp. 233-240.
Bischoff et al, A homologue of *Drosophila aurora* kinase is oncogenic and amplified in human colorectal cancers, EMBO; 1998 (17) 11 pp. 3052-3065.
Cary et al, Stimulation of cell migration by overexpression of focal adhesion kinase and its association with Src and Fyn, Journal of Cell Science, 1996 (109), pp. 1787-1794.
Chen et al, Association of focal adhesion kinase with its potential substrate phosphatidylinositol 3-kinase, Proc. Natl. Acad. Sci. USA, 1994 (91), pp. 10148-10152.
Davies et al, Inhibitor Binding to Active and Inactive CDK2: The Crystal Structure of CDK2-Cyclin A/Indirubin-5-Sulphonate, Structure, 2001 (9) pp. 389-397.
Davis et al, Isolation of Angiopoietin-1, a Ligand for the TIE2 Receptor, by Secretion-Trap Expression Cloning, Cell, 1996 (87) pp. 1161-1169.
Dumont et al, Dominant-negative and targeted null mutations in the endothelial receptor tyrosine kinase, tek, reveal a critical role in vasculogenesis of the embryo, Genes Dev., 1994 (8) pp. 1897-1909.
Kornberg et al, Cell Adhesion or Integrin Clustering Increases Phosphorylation of a Focal Adhesion-associated Tyrosine Kinase, J. Biol. Chem., 1992 (267) 33, pp. 23439-23442.
Lee et al, Anti-Vascular Endothelial Growth Factor Treatment Augments Tumor Radiation Response under Normoxic or Hypoxic Conditions 1, Cancer Research, 2000 (60) 19 pp. 5565-5570.
Lin et al, antiangiogenic gene therapy targeting the endothelium-specific receptor tyrosine kinase Tie2, PNAS, 1998 (95) pp. 8829-8834.
Lin et al, Inhibition of Tumor Anglogenesis Using a soluble Receptor Establishes a Role for Tie2 in Pathologic Vascular Growth, J. Clin. Invest., 1997 (100) 8 pp. 2072-2078.

(Continued)

*Primary Examiner* — D. Margaret Seaman
*Assistant Examiner* — Niloofar Rahmani
(74) *Attorney, Agent, or Firm* — Scully, Scott, Murphy & Presser, P.C.

(57) ABSTRACT

The invention relates to compounds of formula (I):

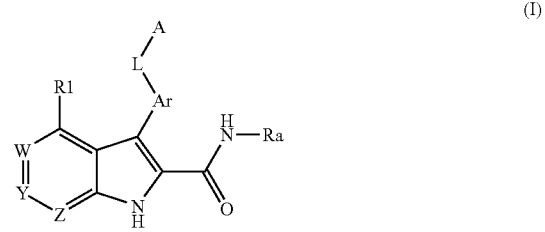

wherein Ra, R1, Ar, L, A, W, Y, and Z are as defined in the disclosure; to compositions containing them; and to the preparation and use thereof, in particular as anticancer agents.

24 Claims, No Drawings

OTHER PUBLICATIONS

Ling et al, Malignant Astrocytoma Cell Attachment and Migration to Various Matrix Proteins Is Differentially Sensitive to Phosphoinositide 3-OH Kinase Inhibitors, J. Cell. Biochemistry, 1999 (73), pp. 533-544.

Maisonpierre et al, Angiopoietin-2, a Natural Antagonist for Tie2 That Disrupts in vivo Angiogenesis, Science, 1997 (277) pp. 55-60.

Maung et al, requirement for focal adhesion kinase in tumor cell adhesion, Oncogene,1999 (18),pp. 6824-6828.

Millauer et al, Dominant-Negative Inhibition of Flk-1 Suppresses the Growth of Many Tumor Types in Vivo, Cancer Research, 1996 (56) pp. 1615-1620.

Oktay et al, Integrin-mediated Activation of Focal Adhesion Kinase Is Required for Signaling to Jun NH2-terminal Kinase and Progression through the G1 Phase of the Cell Cycle, J. Cell. Biol., 1999 (145) 7 pp. 1461-1469.

Owens et al, Overexpression of the Focal Adhesion Kinase (p125 FAK) in Invasive Human Tumors 1, Cancer Research, 1995 (55), pp. 2752-2755.

Richardson et al, A mechanism for regulation of the adhesion-associated protein tyrosine kinase pp125 FAK, Nature, 1996 (380), pp. 538-540.

Roy et al, Early Development of Cyclin Dependent Kinase Modulators, Current Pharmaceutical Design, 2001 (7) pp. 1669-1687.

Schaller et al, Autophosphorylation of the Focal Adhesion Kinase, pp125 FAK, Directs SH2-Dependent Binding of pp60src, Mol. Cell. Biol., 1994 (14), pp. 1680-1688.

Schlaepfer et al, Focal Adhesion Kinase Overexpression Enhances Ras-dependent Integrin Signaling to ERK2/Mitogen-activated Protein Kinase through Interactions with and Activation of c-Src, J. Biol. Chem., 1997 (272) 20, pp. 13189-13195.

Schlaepfer et al, Integrin-mediated signal transduction linked to Ras pathway by GRB2 binding to focal adhesion kinase, Nature, 1994 (372) 22, pp. 786-791.

Schlaepfer et al, Signaling through focal adhesion kinase, Prog. Biophy. Mol. Biol., 1999 (71), pp. 435-478.

Sieg et al, Required role of focal adhesion kinase (FAK) for integrin-stimulated cell migration, J. Cell Science, 1999 (112), pp. 2677-2691.

Strawn et.al, Flk-1 as a Target for Tumor Growth Inhibition, Cancer Research, 1996 (56) pp. 3540-3545.

Suri et al, Requisite Role of Angiopoietin-1, a Ligand for the TIE2 Receptor, during Embryonic Angiogenesis, Cell, 1996 (87) pp. 1171-1180.

Toogood, Cyclin-Dependent Kinase Inhibitors for Treating Cancer, Med. Res. Rev., 2001 (21) 6 pp. 487-498.

Vuori et al, Induction of p130cas Signaling Complex Formation upon Integrin-Mediated Cell Adhesion: a Role for Src Family Kinases, Mol. Cell. Biol., 1996 (16) 6, pp. 2606-2613.

Wang et al, p125 focal adhesion kinase promotes malignant astrocytoma cell proliferation in vivo, J. Cell Sci., 2000 (113), pp. 4221-4230.

Weiner et al, Expression of focal adhesion kinase gene and Invasive cancer, Lancet., 1993 (342), pp. 1024-1025.

Xing et al, Direct Interaction of v-Src with the Focal Adhesion Kinase Mediated by the Src SH2 Domain, Mol. Biol. of the Cell, 1994 (5), pp. 413-421.

Xu et al, Attenuation of the Expression of the Focal Adhesion Kinase Induces Apoptosis in Tumor Cells, Cell Growth Diff., 1996 (7), pp. 413-418.

Zhao et al, Regulation of the Cell Cycle by Focal Adhesion Kinase, J. Cell. Biol., 1998 (143) 7, pp. 1997-2008.

* cited by examiner

SUBSTITUTED PYRROLOPYRIDINES, COMPOSITIONS CONTAINING THEM, MANUFACTURING PROCESS THEREFOR AND USE THEREOF

The present invention relates especially to novel chemical compounds, particularly substituted pyrrolopyridines, to compositions containing the same and to the use thereof as medicaments.

More particularly, and according to a first aspect, the invention relates to novel specific substituted pyrrolopyridines with anticancer activity, via modulation of the activity of proteins, in particular kinases.

To date, most of the commercial compounds used in chemotherapy pose major problems of side effects and of patient tolerance. These effects could be limited if the medicaments used acted selectively on cancer cells, to the exclusion of healthy cells. One of the solutions for limiting the adverse effects of a chemotherapy may thus consist in using medicaments that act on metabolic pathways or constituent elements of these pathways, predominantly expressed in the cancer cells, and which are sparingly expressed or not expressed in healthy cells.

Protein kinases are a family of enzymes that catalyse the phosphorylation of hydroxyl groups of specific residues of proteins such as tyrosine, serine or threonine residues. Such phosphorylations can largely modify the function of proteins; thus, protein kinases play an important role in regulating a wide variety of cell processes, especially including metabolism, cell proliferation, cell differentiation, cell migration or cell survival. Among the various cellular functions in which the activity of a protein kinase is involved, certain processes represent attractive targets for treating cancer diseases and also other diseases.

Thus, one of the objects of the present invention is to propose compositions with anticancer activity, by acting in particular with respect to kinases. Among the kinases for which a modulation of activity is desired, KDR and Tie2 are preferred.

These products correspond to formula (I) below:

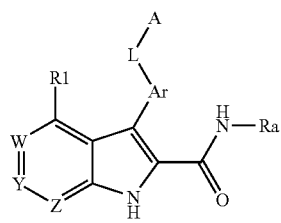

Formula (I)

in which:
1) A and Ar are independently selected from the group consisting of: aryl, heteroaryl, heterocyclyl, cycloalkyl, substituted aryl, substituted heteroaryl, substituted heterocyclyl, substituted cycloalkyl;
2) L is selected from the group consisting of: bond, CO, NH, CO—NH, NH—CO, NH—SO, NH—SO$_2$, SO$_2$NH, NH—CH$_2$, CH$_2$—NH, CH$_2$—CO—NH, NH—CO—CH$_2$, NH—CH$_2$—CO, CO—CH$_2$—NH, NH—CO—NH, NH—CS—NH, NH—CO—O, O—CO—NH;
3) one from among Y and Z is chosen from N and NO, and the other from among Y and Z is C(R5), and W is C(R6);
4) R1, R5, and R6 are each independently chosen from the group consisting of: H, halogen, R2, CN, O(R2), OC(O)(R2), OC(O)N(R2)(R3), OS(O$_2$)(R2), N(R2)(R3), N=C(R2)(R3), N(R2)C(O)(R3), N(R2)C(O)O(R3), N(R4)C(O)N(R2)(R3), N(R4)C(S)N(R2)(R3), N(R2)S(O$_2$)(R3), C(O)(R2), C(O)O(R2), C(O)N(R2)(R3), C(=N(R3))(R2), C(=N(OR3))(R2), S(R2), S(O)(R2), S(O$_2$)(R2), S(O$_2$)O(R2), S(O$_2$)N(R2)(R3); in which each R2, R3, R4 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl, substituted heterocyclyl, alkylene, substituted alkylene, substituted alkynyl; in which, when R2 and R3 are simultaneously present on one of the groups R1, R5 and R6, they may be linked together to form a ring;
5) Ra is selected from the group consisting of H, (C1-C4) alkyl and (C3-C4)cycloalkyl.

Ra is advantageously H.

R1, R5 and R6 are selected from H, halogen, OMe and methyl; preferably from H and F, and even more preferentially R1, R5 and R6 are H. Acceptable combinations of substituents include those in which R1, R5 and R6 are H and one from among Y and Z is chosen from N and NO.

A substituent Ar according to the invention may be chosen from phenyl, pyridyl, thienyl, furyl and pyrrolyl, substituted with R11, in which R11 has the same definition as R5. R11 is preferably selected from the group consisting of H, F, Cl, methyl, NH$_2$, OCF$_3$ and CONH$_2$.

A substituent Ar is preferentially an unsubstituted phenyl.

A substituent L-A according to the invention may be chosen from NH—CO—NH-A and NH—SO$_2$-A, in particular NH—CO—NH-A.

A substituent A according to the invention may be selected from the group consisting of phenyl, pyridyl, pyrimidyl, thienyl, furyl, pyrrolyl, oxazolyl, thiazolyl, isoxazolyl, isothiazolyl, pyrazolyl, imidazolyl, indolyl, indazolyl, benzimidazolyl, benzoxazolyl, and benzothiazolyl; optionally substituted.

A preferred substituent A is chosen from phenyl, pyrazolyl and isoxazolyl; optionally substituted. A more preferred substituent A is phenyl.

A is advantageously substituted with a first substituent selected from the group consisting of alkyl, haloalkyl, cycloalkyl, alkylene, alkynyl, aryl, heteroaryl, O-alkyl, O-aryl, O-heteroaryl, S-alkyl, S-aryl and S-heteroaryl, each being optionally substituted with a substituent chosen from (C1-C3)alkyl, halogen, O—(C1-C3)alkyl, N(R8)(R9); in which R8 and R9 are independently chosen from H, (C1-C3) alkyl, (C1-C3)alkylOH, (C1-C3)haloalkyl, (C1-C3)alkylNH$_2$, (C1-C3)alkylCOOM, (C1-C3)alkylSO$_3$M; in which, when R8 and R9 are simultaneously other than H, they may be linked to form a 5- to 7-membered ring comprising from 0 to 3 heteroatoms chosen from O, N and S, in which M is H or a cation of an alkali metal chosen from Li, Na and K.

In addition, A is also advantageously substituted with a second substituent selected from the group consisting of F, Cl, Br, I, OH, SH, SO$_3$M, COOM, CN, NO$_2$, CON(R8)(R9), N(R8)CO(R9), (C1-C3)alkyl-OH, (C1-C3)alkyl-N(R8)(R9), (C1-C3)alkyl-(R10), (C1-C3)alkyl-COOH, N(R8)(R9); in which R8 and R9 are independently chosen from H, (C1-C3) alkyl, (C1-C3)alkylOH, (C1-C3)haloalkyl, (C1-C3)alkylNH$_2$, (C1-C3)alkylCOOM, (C1-C3)alkylSO$_3$M; in which, when R8 and R9 are simultaneously other than H, they may be linked to form a 5- to 7-membered ring comprising from 0 to 3 heteroatoms chosen from O, N and S; in which M is H or a cation of an alkali metal chosen from Li, Na and K; and in which R10 is H or an optionally substituted non-aromatic heterocycle containing 2 to 7 carbon atoms and 1 to 3 heteroatoms chosen from N, O and S.

When A is disubstituted, the two substituents may be linked together to form a 5- to 7-membered ring containing from 0 to 3 heteroatoms chosen from N, O and S.

According to one preferred embodiment, A is phenyl, pyrazolyl or isoxazolyl substituted with at least one group chosen from halogen, (C1-C4)alkyl, (C1-C3)haloalkyl, O—(C1-C4)alkyl, S—(C1-C4)alkyl, O—(C1-C4)haloalkyl, S—(C1-C4)haloalkyl, and in which, when A is disubstituted, the two substituents may be linked together to form a 5- to 7-membered ring containing from 0 to 3 heteroatoms chosen from N, O and S.

The products according to the invention may be:
1) in non-chiral form, or
2) in racemic form, or
3) enriched in one stereoisomer, or
4) enriched in one enantiomer;
and may optionally be salified.

A product in accordance with the invention may be used for the manufacture of a medicament that is useful for treating a pathological condition, in particular a cancer.

The present invention also relates to a medicament comprising a product according to the invention, and to therapeutic compositions comprising a product according to the invention in combination with a pharmaceutically acceptable excipient according to the chosen mode of administration. The pharmaceutical composition may be in solid or liquid form or in the form of liposomes.

Among the solid compositions that may be mentioned are powders, gel capsules and tablets. Among the oral forms that may also be included are solid forms protected with respect to the acidic medium of the stomach. The supports used for the solid forms consist especially of mineral supports, for instance phosphates or carbonates, or organic supports, for instance lactose, celluloses, starch or polymers. The liquid forms consist of solutions, suspensions or dispersions. They contain as dispersive support either water or an organic solvent (ethanol, NMP or the like) or mixtures of surfactants and of solvents, or of complexing agents and of solvents.

The liquid forms will preferably be injectable and, as a result, will have a formulation that is acceptable for such a use.

Routes of administration that are acceptable by injection include intravenous, intraperitoneal, intramuscular and subcutaneous routes, the intravenous route usually being preferred.

The administered dose of the compounds of the invention will be adapted by the practitioner as a function of the route of administration to the patient and of the patient's condition.

The compounds of the present invention may be administered alone or as a mixture with other anticancer agents. Among the possible combinations that may be mentioned are:

alkylating agents and especially cyclophosphamide, melphalan, ifosfamide, chlorambucil, busulfan, thiotepa, prednimustine, carmustine, lomustine, semustine, streptozotocin, decarbazine, temozolomide, procarbazine and hexamethylmelamine platinum derivatives such as, especially, cisplatin, carboplatin or oxaliplatin antibiotics such as, especially, bleomycin, mitomycin or dactinomycin antimicrotubule agents such as, especially, vinblastine, vincristine, vindesine, vinorelbine and taxoids (paclitaxel and docetaxel)

anthracyclines such as, especially, doxorubicin, daunorubicin, idarubicin, epirubicin, mitoxantrone and losoxantrone group I and II topoisomerase inhibitors such as etoposide, teniposide, amsacrine, irinotecan, topotecan and tomudex fluoropyrimidines such as 5-fluorouracil, UFT and floxuridine cytidine analogues such as 5-azacytidine, cytarabine, gemcitabine, 6-mercaptomurine and 6-thioguanine adenosine analogues such as pentostatin, cytarabine or fludarabine phosphate methotrexate and folinic acid various enzymes and compounds such as L-asparaginase, hydroxyurea, trans-retinoic acid, suramine, dexrazoxane, amifostine and herceptin, and also oestrogen-based and androgenic hormones antivascular agents such as combretastatin derivatives, for example CA4P, chalcone or colchicine derivatives, for example ZD6126, and prodrugs thereof.

It is also possible to combine the compounds of the present invention with a radiation treatment. These treatments may be administered simultaneously, separately or sequentially. The treatment will be adapted by the practitioner as a function of the patient to be treated.

The products of the invention are useful as inhibitors of a reaction catalysed by a kinase, in particular FAK, KDR, Tie2, Aurora A, Aurora B and CDK2. FAK, KDR and Tie2 are kinases for which the products of the invention will be particularly useful as inhibitors.

The reasons for which these kinases are chosen are given below:

FAK

FAK is a cytoplasmic tyrosine kinase that plays an important role in transducing the signal transmitted by the integrins, a family of heterodimeric cellular adhesion receptors. FAK and the integrins are colocated in perimembrane structures known as adhesion plaques. It has been shown in many cell types that the activation of FAK and its phosphorylation on tyrosine residues and in particular its autophosphorylation on tyrosine 397 were dependent on the binding of integrins to their extracellular ligands and thus induced during cellular adhesion [Kornberg L. et al. J. Biol. Chem. 267(33): 23439-442. (1992)]. Autophosphorylation on tyrosine 397 of FAK represents a binding site for another tyrosine kinase, Src, via its SH2 domain [Schaller et al. Mol. Cell. Biol. 14: 1680-1688. 1994; Xing et al. Mol. Cell. Biol. 5: 413-421. 1994]. Src may then phosphorylate FAK on tyrosine 925, thus recruiting the adapter protein Grb2 and inducing in certain cells activation of the ras and MAP kinase pathway involved in controlling cell proliferation [Schlaepfer et al. Nature; 372: 786-791. 1994; Schlaepfer et al. Prog. Biophy. Mol. Biol. 71: 435-478. 1999; Schlaepfer and Hunter, J. Biol. Chem. 272: 13189-13195. 1997]. The activation of FAK may also induce the jun NH2-terminal kinase (JNK) signalling pathway and result in the progression of cells towards the G1 phase of the cell cycle [Oktay et al., J. Cell. Biol. 145: 1461-1469. 1999]. Phosphatidylinositol-3-OH kinase (PI3-kinase) also binds to FAK on tyrosine 397 and this interaction might be necessary for activating PI3-kinase [Chen and Guan, Proc. Nat. Acad. Sci. USA. 91: 10148-10152. 1994; Ling et al. J. Cell. Biochem. 73: 533-544. 1999]. The FAK/Src complex phosphorylates various substrates, for instance paxillin and p130CAS in fibroblasts [Vuori et al. Mol. Cell. Biol. 16: 2606-2613. 1996].

The results of numerous studies support the hypothesis that FAK inhibitors might be useful in treating cancer. Studies have suggested that FAK might play an important role in cell proliferation and/or survival in vitro. For example, in CHO cells, some authors have demonstrated that the overexpression of p125FAK leads to an acceleration of the transition G1 to S, suggesting that p125FAK promotes cell proliferation [Zhao J.-H. et al. J. Cell Biol. 143: 1997-2008. 1998]. Other authors have shown that tumour cells treated with FAK antisense oligonucleotides lose their adhesion and enter into apoptosis (Xu et al., Cell Growth Differ. 4: 413-418. 1996). It has also been demonstrated that FAK promotes the migration of cells in vitro. Thus, fibroblasts that are deficient for FAK expression (FAK "knockout" mice) show a rounded morphology and deficiencies in cellular migration in response to chemotactic signals, and these defects are eliminated by re-expression of FAK [D. J. Sieg et al., J. Cell Science. 112: 2677-91.1999]. Overexpression of the C-terminal domain of FAK (FRNK) blocks the stretching of adherent cells and reduces cell migration in vitro [Richardson A. and Parsons J. T. Nature. 380: 538-540. 1996]. Overexpression of FAK in CHO or COS cells or in human astrocytoma cells promotes migration of the cells. The involvement of FAK in promotion of the proliferation and migration of cells in many cell types in vitro suggests the potential role of FAK in neoplastic processes. A recent study has effectively demonstrated the increase in the proliferation of tumour cells in vivo after inducing the expression of FAK in human astrocytoma cells [Cary L. A. et al. J. Cell Sci. 109: 1787-94. 1996; Wang D. et al. J. Cell Sci. 113: 4221-4230. 2000]. Furthermore, immunohistochemical studies of human biopsies have demonstrated that FAK was overexpressed in prostate cancer, breast cancer, thyroid cancer, colon cancer, melanoma, brain cancer and lung cancer, the level of expression of FAK being directly correlated to the tumours showing the most aggressive phenotype [Weiner T. M. et al. Lancet. 342 (8878): 1024-1025. 1993; Owens et al. Cancer Research. 55: 2752-2755. 1995; Maung K. et al. Oncogene. 18: 6824-6828. 1999; Wang D. et al. J. Cell Sci. 113: 4221-4230.2000].

KDR

KDR (Kinase insert Domain Receptor), also known as VEGF-R2 (Vascular Endothelial Growth Factor Receptor 2), is expressed solely in endothelial cells. This receptor binds to the angiogenic growth factor VEGF, and thus serves as a transduction signal mediator via the activation of its intracellular kinase domain. The direct inhibition of the kinase activity of VEGF-R2 makes it possible to reduce the phenomenon of angiogenesis in the presence of exogenous VEGF (Vascular Endothelial Growth Factor) (Strawn et al., Cancer Research, 1996, vol. 56, p. 3540-3545). This process has especially been demonstrated using VEGF-R2 mutants (Millauer et al., Cancer Research, 1996, vol. 56, p. 1615-1620). The VEGF-R2 receptor appears to have no other function in adults than that associated with the angiogenic activity of VEGF. Thus, a selective inhibitor of the kinase activity of VEGF-R2 should show only little toxicity.

In addition to this central role in the dynamic angiogenic process, recent results suggest that the expression of VEGF contributes towards the survival of tumoral cells after chemotherapy and radiotherapy, underlining the potential synergy of KDR inhibitors with other agents (Lee et al. Cancer Research, 2000, vol. 60, p. 5565-5570).

Tie2

Tie-2 (TEK) is a member of a family of tyrosine kinase receptors, which is specific to endothelial cells. Tie2 is the first receptor with tyrosine kinase activity for which both the agonist (angiopoietin 1 or Ang1), which stimulates the autophosphorylation of the receptor and cell signalling [S. Davis et al. (1996) Cell 87, 1161-1169], and the antagonist (angiopoietin 2 or Ang2) [P. C. Maisonpierre et al. (1997) Science 277, 55-60] are known. Angiopoietin 1 can synergize with VEGF in the final stages of neoangiogenesis [Asahara T. Circ. Res. (1998) 233-240]. Knock-out experiments and transgenic manipulations of the expression of Tie2 or of Ang1 lead to animals that present vascularization defects [D. J. Dumont et al. (1994) Genes Dev. 8, 1897-1909 and C. Suri (1996) Cell 87, 1171-1180]. The binding of Ang1 to its receptor leads to autophosphorylation of the kinase domain of Tie2, which is essential for neovascularization and also for the recruitment and interaction of blood vessels with the pericytes and smooth muscle cells; these phenomena contribute towards the maturation and stability of the newly formed blood vessels [P. C. Maisonpierre et al. (1997) Science 277, 55-60]. Lin et al. (1997) J. Clin. Invest. 100, 8: 2072-2078 and Lin P. (1998) PNAS 95, 8829-8834 have shown an inhibition of tumour growth and vascularization, and also a reduction in lung metastases, during adenoviral infections or injections of the extracellular domain of Tie-2 (Tek) into models of melanoma and breast tumour xenografts.

Tie2 inhibitors may be used in situations in which neovascularization takes place inappropriately (i.e. in diabetic retinopathy, chronic inflammation, psoriasis, Kaposi's sarcoma, chronic neovascularization due to macular degeneration, rheumatoid arthritis, infantile haemoangioma and cancers).

The progress of the cell cycle is often governed by cycline-dependent kinases (CDK), which are activated by an interaction with proteins belonging to the cycline family, this activation ending in the phosphorylation of substrates and finally in cell division. In addition, the endogenous inhibitors of the CDKs that are activated (family of INK4 and of KIP/CIP) negatively regulate the activity of CDKs. The growth of normal cells is due to a balance between the CDK activators (cyclines) and the endogenous inhibitors of CDKs. In several types of cancer, the aberrant expression or activity of several of these cell cycle regulators has been described.

Cycline E activates the kinase Cdk2, which then acts to phosphorylate the protein pRb (retinoblastoma protein) resulting in an irreversible engagement in cell division and transition to the S phase (P. L. Toogood, Medicinal Research Reviews (2001), 21(6); 487-498). The kinase CDK2 and possibly CDK3 are necessary for progress into the G1 phase and entry into the S phase. During the formation of a complex with cycline E, they maintain the hyperphosphorylation of pRb to aid the progress from the G1 phase to the S phase. In complexes with cycline A, CDK2 plays a role in inactivating E2F and is necessary for achieving the S phase (T. D. Davies et al. (2001) Structure 9, 389-3).

The CDK1/cycline B complex regulates the progress of the cell cycle between the G2 phase and the M phase. Negative regulation of the CDK/cycline B complex prevents normal cells from entering the S phase before the G2 phase has been correctly and completely terminated (K. K. Roy and E. A. Sausville, Current Pharmaceutical Design, 2001, 7, 1669-1687).

A level of regulation of the activity of CDKs exists. The cycline-dependent activators of kinases (CAK) have a positive action on regulating CDKs. CAK phosphorylates CDKs on the threonine residue to make the target enzyme totally active.

The presence of defects in the molecules involved in the cell cycle results in activation of the CDKs and progression of the cycle; it is normal to wish to inhibit the activity of the CDK enzymes in order to block the cell growth of cancer cells.

Many proteins involved in chromosome segregation and spindle assembly have been identified in yeast and *drosophila*. Disorganization of these proteins leads to the nonsegregation of the chromosomes and to monopolar or disorganized spindles. Among these proteins, certain kinases, including Aurora and Ipl1, originating, respectively, from *drosophila* and from *S. cerevisiae*, are necessary for chromosome segregation and separation of the centrosome. A human analogue of yeast Ipl1 has recently been cloned and characterized by various laboratories. This kinase, known as Aurora2, STK15 or BTAK, belongs to the serine/threonine kinase family. Bischoff et al. have shown that Aurora2 is oncogenic, and is amplified in human colorectal cancers (EMBO J, 1998, 17, 3052-3065). This has also been illustrated in cancers involving epithelial tumours such as breast cancer.

DEFINITIONS

The term "halogen" refers to an element chosen from F, Cl, Br and I.

The term "alkyl" refers to a linear or branched saturated hydrocarbon-based substituent containing from 1 to 12 carbon atoms. The substituents methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 1-ethylbutyl, 2-ethylbutyl, 3,3-dimethylbutyl, heptyl, 1-ethylpentyl, octyl, nonyl, decyl, undecyl and dodecyl are examples of alkyl substituents.

The term "alkylene" refers to a linear or branched hydrocarbon-based substituent containing one or more unsaturations, and containing from 2 to 12 carbon atoms. The substituents ethylenyl, 1-methylethylenyl, prop-1-enyl, prop-2-enyl, Z-1-methylprop-1-enyl, E-1-methylprop-1-enyl, Z-1,2-dimethyl-prop-1-enyl, E-1,2-dimethylprop-1-enyl, but-1,3-dienyl, 1-methylidenylprop-2-enyl, Z-2-methylbut-1,3-dienyl, E-2-methylbut-1,3-dienyl, 2-methyl-1-methylidenylprop-2-enyl, undec-1-enyl and undec-10-enyl are examples of alkylene substituents.

The term "alkynyl" refers to a linear or branched hydrocarbon-based substituent containing at least two unsaturations borne by a pair of vicinal carbon atoms, and containing from 2 to 12 carbon atoms. The substituents ethynyl; prop-1-ynyl; prop-2-ynyl; and but-1-ynyl are examples of alkynyl substituents.

The term "aryl" refers to a monocyclic or polycyclic aromatic substituent containing from 6 to 14 carbon atoms. The substituents phenyl, naphth-1-yl; naphth-2-yl; anthracen-9-yl; 1,2,3,4-tetrahydronaphth-5-yl; and 1,2,3,4-tetrahydronaphth-6-yl are examples of aryl substituents.

The term "heteroaryl" refers to a monocyclic or polycyclic heteroaromatic substituent containing from 1 to 13 carbon atoms and from 1 to 4 heteroatoms. The substituents pyrrol-1-yl; pyrrol-2-yl; pyrrol-3-yl; furyl; thienyl; imidazolyl; oxazolyl; thiazolyl; isoxazolyl; isothiazolyl; 1,2,4-triazolyl; oxadiazolyl; thiadiazolyl; tetrazolyl; pyridyl; pyrimidyl; pyrazinyl; 1,3,5-triazinyl; indolyl; benzo[b]furyl; benzo[b]thienyl; indazolyl; benzimidazolyl; azaindolyl; quinolyl; isoquinolyl; carbazolyl; and acridyl are examples of heteroaryl substituents.

The term "heteroatom" refers herein to an at least divalent atom other than carbon. N; O; S; and Se are examples of heteroatoms.

The term "cycloalkyl" refers to a saturated or partially unsaturated cyclic hydrocarbon-based substituent containing from 3 to 12 carbon atoms. The substituents cyclopropyl; cyclobutyl; cyclopentyl; cyclopentenyl; cyclopenta-dienyl; cyclohexyl; cyclohexenyl; cycloheptyl; bicyclo[2.2.1]heptyl; cyclooctyl; bicyclo[2.2.2]octyl; adamantyl; and perhydronaphthyl are examples of cycloalkyl substituents.

The term "heterocyclyl" refers to a saturated or partially unsaturated cyclic hydrocarbon-based substituent containing from 1 to 13 carbon atoms and from 1 to 4 heteroatoms. Preferably, the saturated or partially unsaturated cyclic hydrocarbon-based substituent will be monocyclic and will contain 4 or 5 carbon atoms and 1 to 3 heteroatoms.

The term "substituted" refers to one or more substituents other than H, for example halogen; alkyl; aryl; heteroaryl, cycloalkyl; heterocyclyl; alkylene; alkynyl; OH; O-alkyl; O-alkylene; O-aryl; O-heteroaryl; NH$_2$; NH-alkyl; NH-aryl; NH-heteroaryl; N-alkyl-alkyl'; SH; S-alkyl; S-aryl; S(O$_2$)H; S(O$_2$)-alkyl; S(O$_2$)-aryl; SO$_3$H; SO$_3$-alkyl; SO$_3$-aryl; CHO; C(O)-alkyl; C(O)-aryl; C(O)OH; C(O)O-alkyl; C(O)O-aryl; OC(O)-alkyl; OC(O)-aryl; C(O)NH$_2$; C(O)NH-alkyl; C(O)NH-aryl; NHCHO; NHC(O)-alkyl; NHC(O)-aryl; NH-cycloalkyl; NH-heterocyclyl.

The products according to the invention may be prepared using conventional methods of organic chemistry. Scheme 1 below illustrates the method used for the preparation of Example 1 concerning the substituted 6-aza-indoles. In this respect, it cannot constitute a limitation of the scope of the invention, as regards the methods for preparing the claimed compounds. Preparation of the 6-aza-indole-2-carboxamide derivatives substituted in position 3:

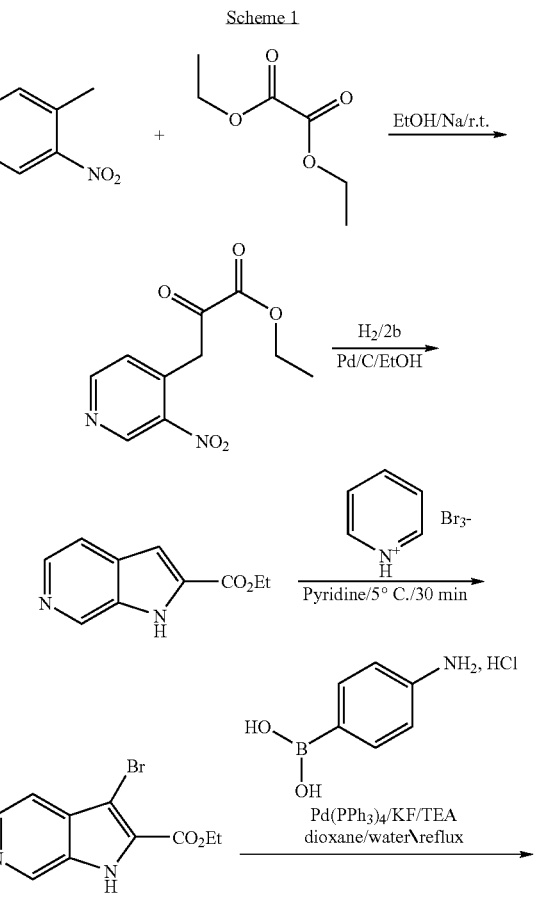

Scheme 1

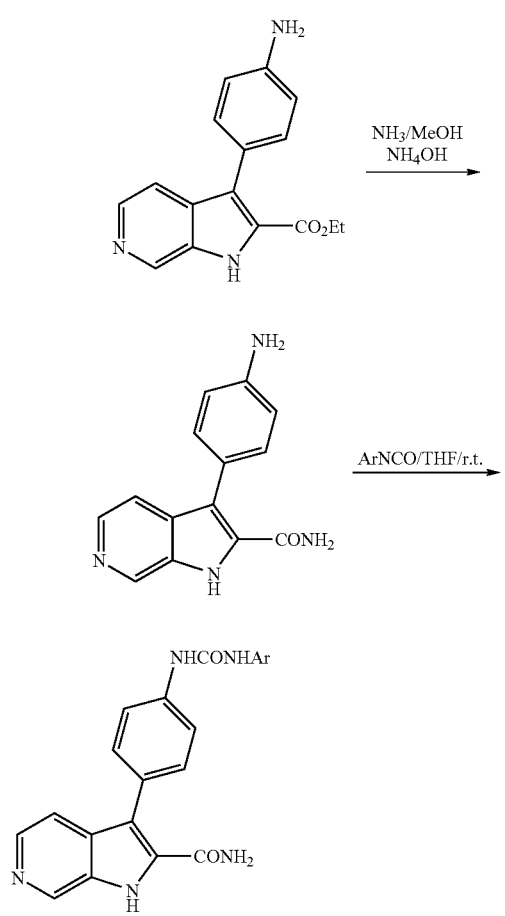

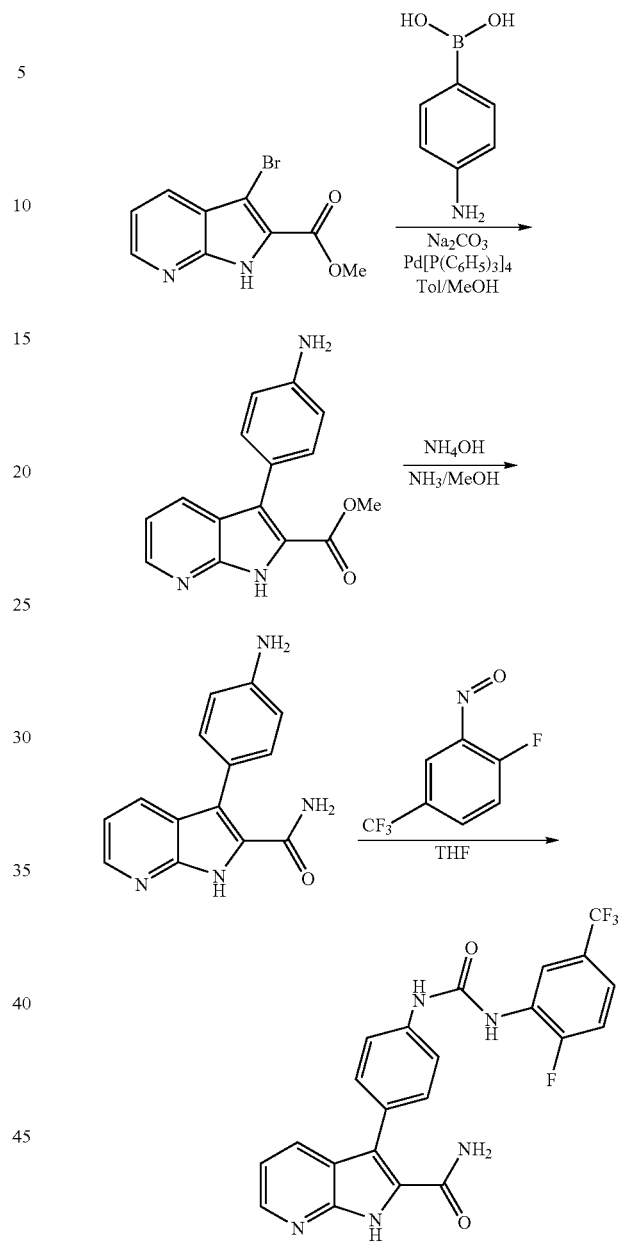

Scheme 2 below illustrates the method used for preparing the examples concerning the substituted 7-aza-indoles, in particular Example 7. In this respect, it cannot constitute a limitation of the scope of the invention, as regards the methods for preparing the claimed compounds. Preparation of the 7-aza-indole-2-carboxamide derivatives substituted in position 3:

Scheme 2

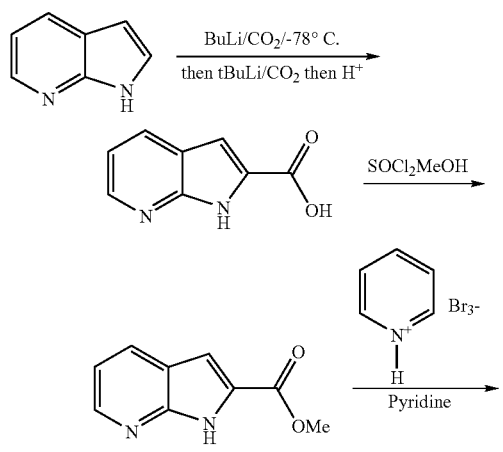

The products of general formula (I) in which Ra is other than H may be obtained according to the conventional methods known to those skilled in the art, for example by replacing ammonia in the aminolysis with the corresponding primary alkylamine.

A subject of the present invention is also a process for preparing the products of formula (I) as defined above, characterized in that a product of general formula (V) below:

(V)

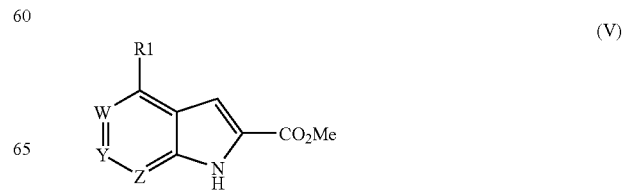

undergoes the following steps:
a) halogenation in position 3, followed by
b) Suzuki coupling in position 3, to obtain a product of general formula (III) below:

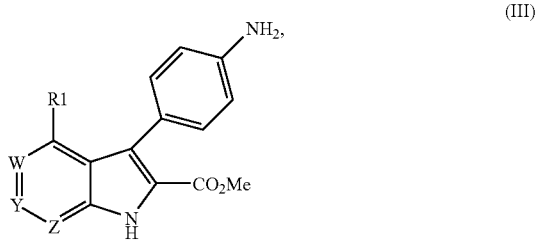

(III)

followed by
c) amidation of the ester in position 2 to obtain the product of general formula (II) below:

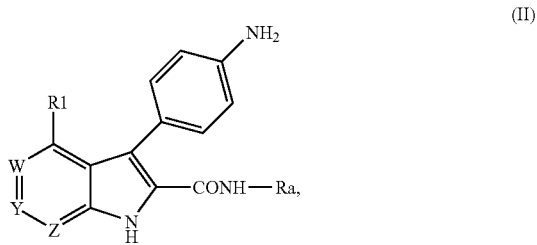

(II)

followed by
d) acylation of the aminophenyl group in position 3.

A subject of the present invention is also, as intermediate products, the compounds of general formula (II) below:

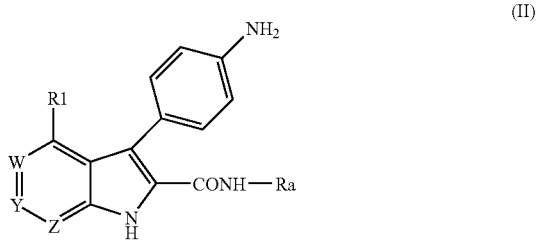

(II)

in which Z, Y and W are as defined above, for the preparation of the products of general formula (I).

The LC/MS analyses were performed on an LCT Micromass machine connected to an HP 1100 machine. The abundance of the products was measured using an HP G1315A diode array detector over a wavelength range of 200-600 nm and a Sedex 65 light scattering detector. The mass spectra were acquired over a range from 180 to 800. The data were analysed using the Micromass MassLynx software. The separation was performed on a Hypersil BDS C18, 3 μm (50×4.6 mm) column, eluting with a linear gradient of 5% to 90% acetonitrile containing 0.05% (v/v) of trifluoroacetic acid (TFA) in water containing 0.05% (v/v) of TFA, over 3.5 minutes at a flow rate of 1 ml/minute. The total analysis time, including the column reequilibration period, is 7 minutes.

The mass spectra were acquired in electrospray (ES+) mode on a Platform II (Micromass) machine. The main ions observed are described.

The melting points were measured by capillary, on a Mettler FP62 machine, over the range 30° C. to 300° C., with a temperature rise of 2° C. per minute.

Purification by LC/MS:

The products may be purified by LC/MS using a Waters FractionsLynx system composed of a Waters 600 gradient pump, a Waters 515 regeneration pump, a Waters Reagent Manager dilution pump, a Waters 2700 auto-injector, two Rheodyne LabPro valves, a Waters 996 diode array detector, a Waters ZMD mass spectrometer and a Gilson 204 fraction collector. The system was controlled by the Waters FractionLynx software. The separation was performed alternately on two Waters Symmetry ($C_{18}$, 5 μM, 19×50 mm, catalogue reference 186000210) columns, one column undergoing regeneration with a 95/5 (v/v) water/acetonitrile mixture containing 0.07% (v/v) of trifluoroacetic acid, while the other column was being used for separation. The columns were eluted using a linear gradient of 5% to 95% acetonitrile containing 0.07% (v/v) of trifluoroacetic acid in water, at a flow rate of 10 ml/minute. On leaving the separation column, one thousandth of the effluent is separated out using an LC Packing Accurate machine, diluted with methanol at a flow rate of 0.5 ml/minute and conveyed to the detectors, in a proportion of 75% to the diode array detector and the remaining 25% to the mass spectrometer. The rest of the effluent (999/1000) is conveyed to the fraction collector, where the flow is discarded if the mass of the expected product is not detected by the FractionLynx software. The molecular formulae of the expected products are supplied to the FractionLynx software, which triggers the collection of the product when the mass signal detected corresponds to the $[M+H]^+$ ion and/or to the $[M+Na]^+$ ion. In certain cases, depending on the analytical LC/MS results, when an intense ion corresponding to $[M+2H]^{++}$ was detected, the value corresponding to half the calculated molecular mass (MW/2) is also supplied to the FractionLynx software. Under these conditions, collection is also triggered when the mass signal of the $[M+2H]^{++}$ and/or $[M+Na+H]^{++}$ ion is detected. The products were collected in tared glass tubes. After collection, the solvents were evaporated off, in a Savant AES 2000 or Genevac HT8 centrifugal evaporator and the masses of the products were determined by weighing the tubes after evaporation of the solvents.

Another subject of the invention relates to the products of the examples below, which illustrate the present invention in a non-limiting manner.

EXAMPLE 1

3-{4-[3-(2-Fluoro-5-trifluoromethylphenyl)ureido]phenyl}-1H-pyrrolo[2,3-c]pyridine-2-carboxamide

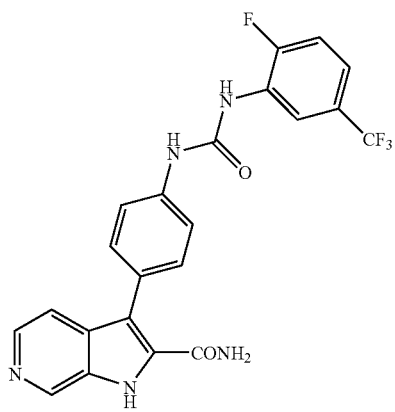

To a solution of 90 mg of 3-(4-aminophenyl)-1H-pyrrolo[2,3-c]pyridine-2-carboxamide in 5 mL of tetrahydrofuran are added dropwise 50 μL of 2-fluoro-5-(trifluoromethyl) phenyl isocyanate. The reaction mixture is stirred for 16 hours at room temperature under an argon atmosphere and then concentrated under reduced pressure. The residue obtained is stirred for 30 minutes in 2 mL of dichloromethane. The suspended solid is filtered off and drained by suction. After drying under vacuum, at 40° C., 115 mg of 3-{4-[3-(2-fluoro-5-trifluoromethylphenyl)ureido]phenyl}-1H-pyrrolo[2,3-c]-pyridine-2-carboxamide are obtained, the characteristics of which are as follows:

IR (KBr): 3455; 1661; 1602; 1542; 1444; 1341; 1312; 1127; 1070 and 819 cm$^{-1}$ $^1$H NMR: 6.98 (broad s, 1H); 7.39 (broad m, 1H); from 7.42 to 7.56 (m, 4H); 7.60 (broad d, J=8.0 Hz, 2H); 7.74 (broad s, 1H); 8.17 (d, J=6.0 Hz, 1H); 8.65 (broad d, J=7.5 Hz, 1H); 8.82 (s, 1H); 8.94 (broad s, 1H); 9.31 (s, 1H); 12.15 (broad s, 1H).

Mass spectrum (ES$^+$): m/z=458 [M+H]$^+$

Melting point: 286° C. (Köfler).

3-(4-Aminophenyl)-1H-pyrrolo[2,3-c]pyridine-2-carboxamide

To a solution of 600 mg of ethyl 3-(4-aminophenyl)-1H-pyrrolo[2,3-c]pyridine-2-carboxylate in 62 mL of a 3N solution of ammonia in methanol are added 11 mL of 22% aqueous ammonia solution. The reaction mixture is stirred for 20 hours in an autoclave at 80° C. (12 bar) and then concentrated under reduced pressure. The residue obtained is diluted in 100 mL of methanol, treated with carbon black and refluxed for 30 minutes. The mixture is filtered while hot through Celite and then rinsed with 2×10 mL of methanol. The filtrate is concentrated under reduced pressure to give 490 mg of 3-(4-aminophenyl)-1H-pyrrolo[2,3-c]pyridine-2-carboxamide in the form of a foam, the characteristics of which are as follows:

Mass spectrum (EI) m/z=252 [M]$^+$, m/z=235 [M−NH$_3$]$^+$

Ethyl 3-(4-aminophenyl)-1H-pyrrolo[2,3-c]pyridine-2-carboxylate

To a solution of 1 g of ethyl 3-bromo-1H-pyrrolo[2,3-c] pyridine-2-carboxylate in 100 mL of dioxane are added 773 mg of 4-aminophenylboronic acid hydrochloride and 1.1 g of potassium fluoride in 9 mL of water. The reaction mixture is stirred under an argon atmosphere for 15 minutes. 425 mg of tetrakis(triphenylphosphine)palladium(0) and 630 μL of triethylamine are added. The reaction mixture is stirred for 17 hours at reflux. After treating with carbon black and then filtering through Celite®, the filtrate is concentrated under reduced pressure. The residue is purified by flash chromatography on a column of silica (60; 35-70 μM), eluting with a mixture of dichloromethane, methanol and acetonitrile (90/5/5 by volume). 600 mg of ethyl 3-(4-aminophenyl)-1H-pyrrolo[2,3-c]pyridine-2-carboxylate are obtained, the characteristics of which are as follows:

Mass spectrum (EI) m/z=281 [M]$^+$, m/z=235 [M−OEt]$^+$

Ethyl 3-bromo-1H-pyrrolo[2,3-c]pyridine-2-carboxylate

To a solution of 2.24 g of ethyl 1H-pyrrolo[2,3-c]pyridine-2-carboxylate in 150 mL of pyridine is added dropwise a solution of 3.53 g of pyridinium tribromide in 30 mL of pyridine, at 5° C. The reaction mixture is then stirred for 16 hours at a temperature in the region of 20° C., and then washed with 500 mL of ice-cold water. The suspension is filtered. The resulting solid is washed with water and then dried in a vacuum oven at 40° C. 1.97 g of ethyl 3-bromo-1H-pyrrolo[2,3-c]pyridine-2-carboxylate are obtained, the characteristics of which are as follows:

Mass spectrum (EI) m/z=269 [M]$^+$, m/z=189 [M−Br]$^+$, m/z=144 [M−OEt]$^+$

Ethyl 1H-pyrrolo[2,3-c]pyridine-2-carboxylate 1.8 g of 10% palladium-on-charcoal are charged into an autoclave, the atmosphere of which is then made inert with a stream of argon. A solution of 6 g of ethyl 3-(3-nitro-4-pyridyl)-2-oxopropionate in 72 mL of absolute ethanol is added. The reaction medium is then stirred for 3 hours at 20° C. under a pressure of 2 bar of hydrogen. The mixture is then filtered through Celite®. The filtrate is concentrated under reduced pressure and oven-dried at 40° C. to give 4 g of ethyl 1H-pyrrolo[2,3-c]pyridine-2-carboxylate, the characteristics of which are as follows:

Mass spectrum (EI) m/z=190 [M$^+$], m/z=144 [M−OEt]$^+$

Ethyl 3-(3-nitro-4-pyridyl)-2-oxopropionate

To a solution of 930 mg of sodium in 50 mL of absolute ethanol are rapidly added 26 mL of diethyl oxalate. The reaction medium is stirred for 15 minutes at 20° C. A solution of 3.8 g of 4-methyl-3-nitropyridine in 50 mL of absolute ethanol is then added dropwise over 1 hour. The reaction medium is stirred for 4 hours at a temperature in the region of 20° C. and then concentrated under reduced pressure. The residue is taken up in 100 mL of ethyl ether and then filtered. The solid is stirred with 40 mL of 5N hydrochloric acid and then filtered, washed with water and dried under vacuum at 40° C. to give 6.2 g of ethyl 3-(3-nitro-4-pyridyl)-2-oxopropionate having the following characteristics:

Mass spectrum (EI) m/z=238 [M$^+$].

EXAMPLE 2

3-{4-[3-(2-Methoxy-5-methylphenyl)ureido]phenyl}-1H-pyrrolo[2,3-c]pyridine-2-carboxamide

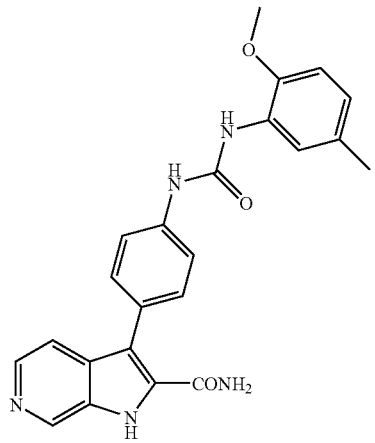

To a solution of 100 mg of 3-(4-aminophenyl)-1H-pyrrolo [2,3-c]pyridine-2-carboxamide in 5 mL of tetrahydrofuran are added dropwise 54.4 μL of 2-methoxy-5-methylphenyl isocyanate. The reaction mixture is stirred for 16 hours at room temperature under an argon atmosphere and then concentrated under reduced pressure. The residue obtained is stirred for 30 minutes in 2 mL of dichloromethane. The suspended solid is filtered off, washed with water and drained by suction. After drying under vacuum, at 40° C., 40 mg of 3-{4-[3-(2-methoxy-5-methylphenyl)ureido]phenyl}-1H-pyrrolo[2,3-c]pyridine-2-carboxamide are obtained, the characteristics of which are as follows:

IR (KBr), 3458; 3331; 1664; 1595; 1537; 1315; 1285; 1213; 1135; 1033 cm$^{-1}$ $^1$H NMR: 2.24 (s, 3H); 3.86 (s, 3H); 6.75 (broad d, J=8.5 Hz, 1H); from 6.85 to 6.95 (m, 2H); 7.43 (broad d, J=8.5 Hz, 2H); 7.46 (d, J=5.5 Hz, 1H); 7.58 (broad d, J=8.5 Hz, 2H); 7.73 (broad s, 1H); 8.02 (broad s, 1H); 8.16 (d, J=5.5 Hz, 1H); 8.22 (s, 1H); 8.82 (s, 1H); 9.44 (broad s, 1H); 12.1 (broad s, 1H).

Mass spectrum (EI): m/z=415 [M$^+$]

Melting point: 227° C.

EXAMPLE 3

3-{4-[3-(3-Chlorophenyl)ureido]phenyl}-1H-pyrrolo[2,3c]pyridine-2-carboxamide trifluoroacetate

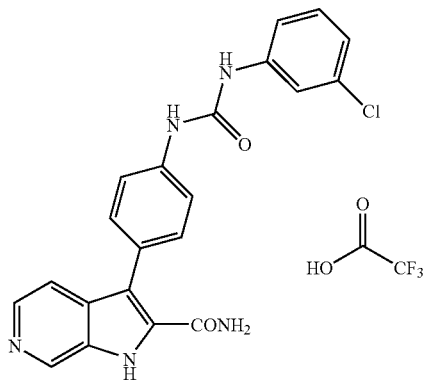

To a solution of 100 mg of 3-(4-aminophenyl)-1H-pyrrolo[2,3-c]pyridine-2-carboxamide in 5 mL of tetrahydrofuran are added dropwise 45.2 µL of 3-chlorophenyl isocyanate. The reaction mixture is stirred for 16 hours at room temperature under an argon atmosphere and then concentrated under reduced pressure. The residue obtained is stirred for 30 minutes in 2 mL of dichloromethane. The suspended solid is filtered off, washed with water and drained by suction. The final purification is performed by preparative LC/MS to give, after drying under vacuum at 40° C., 70 mg of 3-{4-[3-(3-chloro-phenyl)ureido]phenyl}-1H-pyrrolo[2,3-c]pyridine-2-carboxamide in the form of the trifluoroacetate salt, the characteristics of which are as follows:

IR (KBr): 3390; 1672; 1592; 1537; 1483; 1203; 1138; 836; 722 cm$^{-1}$ $^1$H NMR: 7.03 (m, 1H); from 7.26 to 7.34 (m, 2H); from 7.42 to 7.52 (m, 3H); 7.63 (broad d, J=8.5 Hz, 2H); 7.74 (broad s, 1H); 7.97 (d, J=6.0 Hz, 1H); 8.06 (broad s, 1H); 8.31 (d, J=6.0 Hz, 1H); 9.03 (broad s, 2H); 9.13 (s, 1H); 13.35 (broad m, 1H).

Mass spectrum (ES$^+$): m/z=406 [MH$^+$]

Melting point: 221° C.

EXAMPLE 4

3-{4-[3-(3-Chloro-4-fluorophenyl)ureido]phenyl}-1H-pyrrolo[2,3-c]pyridine-2-carboxamide trifluoroacetate

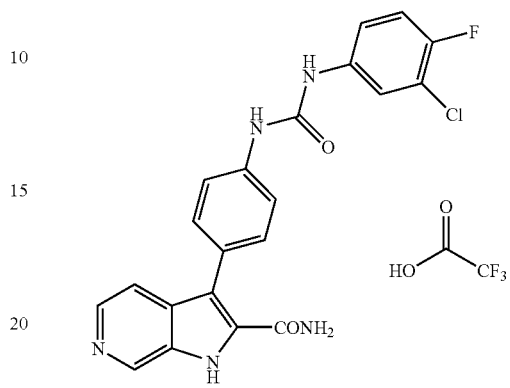

To a solution of 100 mg of 3-(4-aminophenyl)-1H-pyrrolo[2,3-c]pyridine-2-carboxamide in 5 mL of tetrahydrofuran are added dropwise 46.2 µL of 3-chloro-4-fluorophenyl isocyanate. The reaction mixture is stirred for 16 hours at room temperature under an argon atmosphere and then concentrated under reduced pressure. The residue obtained is stirred for 30 minutes in 2 mL of dichloromethane. The suspended solid is filtered off, washed with water and drained by suction. The final purification is performed by preparative LC/MS to give, after drying under vacuum at 40° C., 105 mg of 3-{4-[3-(3-chloro-4-fluorophenyl)ureido]phenyl}-1H-pyrrolo[2,3-c]pyridine-2-carboxamide in the form of the trifluoroacetate salt, the characteristics of which are as follows:

IR (KBr): 3452; 1673; 1601; 1544; 1500; 1208; 1143; 836; 803; 722 cm$^{-1}$ $^1$H NMR: From 7.32 to 7.38 (m, 2H); from 7.44 to 7.54 (m, 3H); 7.64 (broad d, J=8.5 Hz, 2H); 7.84 (broad d, J=7.5 Hz, 1H); 8.01 (d, J=6.0 Hz, 1H); 8.09 (broad s, 1H); 8.32 (d, J=6.0 Hz, 1H); 9.10 (broad s, 2H); 9.16 (s, 1H); 13.4 (broad m, 1H).

Mass spectrum (ES$^+$): m/z=424 [MH$^+$]

Melting point: 214° C.

EXAMPLE 5

3-{4-[3-(2-Fluoro-5-methylphenyl)ureido]phenyl}-1H-pyrrolo[2,3-c]pyridine-2-carboxamide trifluoroacetate

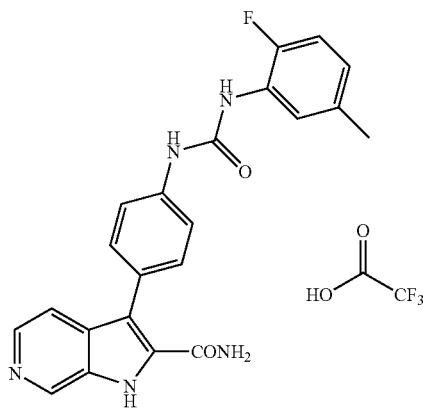

To a solution of 100 mg of 3-(4-aminophenyl)-1H-pyrrolo[2,3-c]pyridine-2-carboxamide in 5 mL of tetrahydrofuran are added dropwise 48.3 μL of 2-fluoro-5-methylphenyl isocyanate. The reaction mixture is stirred for 16 hours at room temperature under an argon atmosphere and then concentrated under reduced pressure. The residue obtained is stirred for 30 minutes in 2 mL of dichloromethane. The suspended solid is filtered off, washed with water and drained by suction. The final purification is performed by preparative LC/MS to give, after drying under vacuum at 40° C., 36 mg of 3-{4-[3-(2-fluoro-5-methylphenyl)ureido]phenyl}-1H-pyrrolo[2,3-c]pyridine-2-carboxamide in the form of the trifluoroacetate salt, the characteristics of which are as follows:

IR (KBr): 3452; 1675; 1603; 1544; 1314; 1202; 1144; 836; 805; 722 cm$^{-1}$ $^1$H NMR: 2.29 (s, 3H); 6.82 (m, 1H); 7.12 (dd, J=8.5 and 11.5 Hz, 1H); from 7.46 to 7.51 (m, 3H); 7.62 (broad d, J=8.5 Hz, 2H); from 7.97 to 8.03 (m, 2H); 8.08 (broad s, 1H); 8.32 (d, J=6.5 Hz, 1H); 8.54 (broad d, J=2.5 Hz, 1H); 9.15 (s, 1H); 9.25 (s, 1H); 13.4 (broad m, 1H)

Mass spectrum (ES$^+$): m/z=404 [MH$^+$]

Melting point: 222° C.

EXAMPLE 6

3-[4-(3-m-Tolylureido)phenyl]-1H-pyrrolo[2,3-c]pyridine-2-carboxamide trifluoroacetate

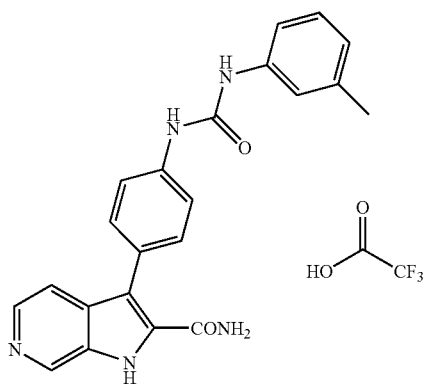

To a solution of 100 mg of 3-(4-aminophenyl)-1H-pyrrolo[2,3-c]pyridine-2-carboxamide in 5 mL of tetrahydrofuran are added dropwise 47.8 μL of m-tolyl isocyanate. The reaction mixture is stirred for 16 hours at room temperature under an argon atmosphere and then concentrated under reduced pressure. The residue obtained is stirred for 30 minutes in 2 mL of dichloromethane. The suspended solid is filtered off, washed with water and drained by suction. The final purification is performed by preparative LC/MS to give, after drying under vacuum at 40° C., 40 mg of 3-[4-(3-m-tolylureido)phenyl]-1H-pyrrolo[2,3-c]pyridine-2-carboxamide in the form of the trifluoroacetate salt, the characteristics of which are as follows:

IR (KBr): 3408; 1699; 1595; 1526; 1203; 1138; 834; 797; 724 cm$^{-1}$ $^1$H NMR: 2.29 (s, 3H); 6.81 (broad d, J=7.5 Hz, 1H); 7.17 (t, J=7.5 Hz, 1H); 7.25 (broad d, J=7.5 Hz, 1H); 7.32 (broad s, 1H); 7.44 (broad s, 1H); 7.47 (broad d, J=8.5 Hz, 2H); 7.62 (broad d, J=8.5 Hz, 2H); 7.96 (broad m, 1H); 8.06 (broad s, 1H); 8.30 (d, J=6.0 Hz, 1H); 8.67 (s, 1H); 8.86 (s, 1H); 9.12 (s, 1H); 13.3 (broad m, 1H).

Mass spectrum (ES$^+$): m/z=386 [MH$^+$]

EXAMPLE 7

3-{4-[3-(2-Fluoro-5-trifluoromethylphenyl)ureido]phenyl}-1H-pyrrolo[2,3-b]pyridine-2-carboxamide

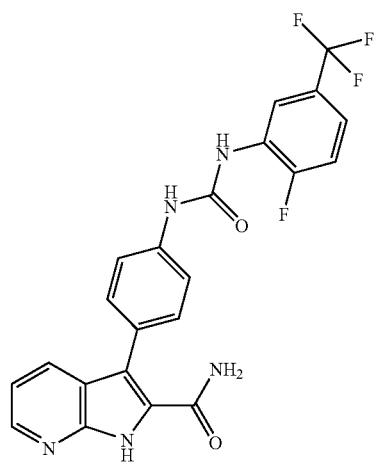

To a solution of 130 mg of 3-(4-aminophenyl)-1H-pyrrolo[2,3-b]pyridine-2-carboxamide in 5 mL of tetrahydrofuran are added dropwise 85 μL of 2-fluoro-5-(trifluoromethyl)phenyl isocyanate. The reaction mixture is then stirred for 16 hours at room temperature under an argon atmosphere and then concentrated under reduced pressure. The residue obtained is chromatographed on a column of silica (eluent: 9/1 dichloromethane/methanol by volume). The fractions containing the expected product are concentrated under reduced pressure. 237 mg of 3-{4-[3-(2-fluoro-5-trifluoromethylphenyl)ureido]phenyl}-1H-pyrrolo[2,3-b]pyridine-2-carboxamide are obtained in the form of a white solid, the characteristics of which are as follows:

IR (KBr): 1659; 1623; 1542; 1443; 1339; 1316; 1119 cm$^{-1}$ $^1$H NMR: 7.08 (broad m, 1H); 7.14 (dd, J=5.0 and 8.0 Hz, 1H); 7.40 (m, 1H); 7.46 (broad d, J=8.5 Hz, 2H); 7.51 (m, 1H); 7.57 (broad d, J=8.5 Hz, 2H); from 7.55 to 7.60 (masked m, 1H); 7.92 (broad d, J=8.0 Hz, 1H); 8.38 (broad d, J=5.0 Hz, 1H); 8.64 (broad d, J=7.5 Hz, 1H); 9.01 (broad s, 1H); 9.36 (broad s, 1H); 12.1 (broad s, 1H).

Mass spectrum (ES$^+$): m/z=458 [M+H$^+$]

Melting point: 232° C. (Köfler).

3-(4-Aminophenyl)-1H-pyrrolo[2,3-b]pyridine-2-carboxamide

To a solution of 260 mg of methyl 3-(4-aminophenyl)-1H-pyrrolo[2,3-b]pyridine-2-carboxylate in 30 mL of a 7N solution of ammonia in methanol are added 5 mL of 22% aqueous ammonia solution. The reaction mixture is then stirred for 20 hours in an autoclave at 80° C. (12.6 bar) and then concentrated under reduced pressure. The residue obtained is chromatographed on a column of silica (eluent: 9/1 dichloromethane/methanol by volume). The fractions containing the expected product are concentrated under reduced pressure. 140 mg of 3-(4-aminophenyl)-1H-pyrrolo[2,3-b]pyridine-2-carboxamide are obtained in the form of a pale yellow solid, the characteristics of which are as follows:

Melting point: 139° C.

Methyl 3-(4-aminophenyl)-1H-pyrrolo[2,3-b]pyridine-2-carboxylate

To a solution of 0.64 g of methyl 3-bromo-1H-pyrrolo[2,3-b]pyridine-2-carboxylate in 50 mL of toluene and 50 ml of methanol are added 1.08 g of 4-aminophenylboronic acid hydrochloride and 0.9 ml of triethylamine. The reaction mixture is then stirred under an argon atmosphere for 15 minutes. 144 mg of tetrakis(triphenylphosphine)palladium(0), 0.3 g of lithium chloride, 0.66 g of sodium carbonate and 7.5 mL of distilled water are successively added. The reaction mixture is stirred for 8 hours at reflux. After filtering through Celite®, the filtrate is concentrated under reduced pressure. The residue is purified by column chromatography on silica, eluting with a mixture of ethyl acetate and cyclohexane (7/3 by volume). 400 mg of methyl 3-(4-aminophenyl)-1H-pyrrolo[2,3-b]pyridine-2-carboxylate are obtained in the form of a yellow solid, the characteristics of which are as follows:

Melting point: 236° C.

Methyl 3-bromo-1H-pyrrolo[2,3-b]pyridine-2-carboxylate

To a solution of 3.2 g of methyl 1H-pyrrolo[2,3-b]pyridine-2-carboxylate hydrochloride in 165 mL of pyridine is added dropwise, at 0° C. under an argon atmosphere, a solution of 5.04 g of pyridinium tribromide in 35 mL of pyridine. The reaction mixture is then stirred at 0° C., and then poured onto a mixture of 250 g of crushed ice and 750 ml of distilled water. The suspension is filtered and the solid is washed with twice 25 mL of distilled water and then dried in the open air. 0.87 g of methyl 3-bromo-1H-pyrrolo[2,3-b]pyridine-2-carboxylate is obtained in the form of a beige-coloured solid, the characteristics of which are as follows:

Mass spectrum (ES$^+$): m/z=256 [M+H$^+$]

Methyl 1H-pyrrolo[2,3-b]pyridine-2-carboxylate hydrochloride

To a solution of 4 g of 1H-pyrrolo[2,3-b]pyridine-2-carboxylic acid hydrochloride in 100 mL of methanol are added dropwise 6 mL of thionyl chloride at room temperature. The reaction mixture is then stirred for 5 hours at room temperature, and then concentrated under reduced pressure. The residue obtained is triturated in 50 mL of ethyl ether and then dried under vacuum at 40° C. 3.22 g of methyl 1H-pyrrolo[2,3-b]pyridine-2-carboxylate hydrochloride are obtained in the form of a pale yellow solid, which is used in unmodified form in the following step.

1H-Pyrrolo[2,3-b]pyridine-2-carboxylic acid hydrochloride

To a solution, cooled to −70° C., of 6.03 g of 1H-pyrrolo[2,3-b]pyridine in 75 ml of anhydrous THF are added dropwise 33 mL of a 1.6M solution of n-butyllithium in hexane. After stirring for 15 minutes at −70° C., 20 g of lumps of cardice are added to the solution. The mixture is then allowed to return to room temperature, and is then concentrated under reduced pressure. 8.4 g of a white solid are obtained, which product is dissolved in 175 mL of tetrahydrofuran. This solution is cooled to −70° C. and 35 mL of a 1.5M solution of t-butyllithium in hexane are then added dropwise. After stirring for 30 minutes at −70° C., 20 g of lumps of cardice are added to the solution. The mixture is then allowed to return to room temperature, and this reaction mixture is then poured into 50 mL of distilled water cooled to 0° C. The tetrahydrofuran is evaporated off under reduced pressure. The residual aqueous solution is diluted with 150 mL of distilled water, washed twice with 100 mL of dichloromethane, acidified to pH 1 by adding 30 mL of aqueous 5N hydrochloric acid solution, and then concentrated under reduced pressure. 10.01 g of a pasty solid are obtained, which is recrystallized from 50 mL of methanol. The solid obtained is treated with a mixture of 50 mL of 7N hydrochloric isopropanol and 50 mL of isopropyl ether. After drying in air, 5.71 g of 1H-pyrrolo[2,3-b]pyridine-2-carboxylic acid hydrochloride are obtained in the form of a cream-coloured solid.

Mass spectrum (EI): m/z=162 [M$^+$]

EXAMPLE 8

3-{4-[3-(2-Fluoro-5-trifluoromethylphenyl)ureido]phenyl}-7-oxy-1H-pyrrolo[2,3-b]pyridine-2-carboxamide

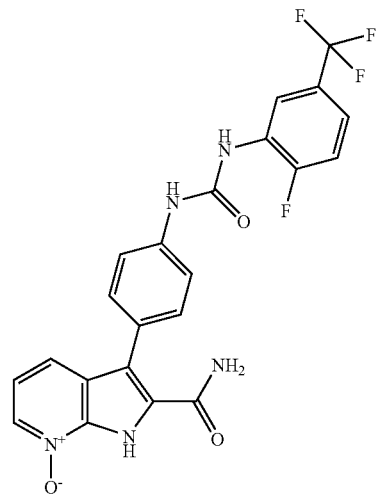

To a solution, maintained at 0° C., of 50 mg of 3-{4-[3-(2-fluoro-5-trifluoromethylphenyl)ureido]phenyl}-1H-pyrrolo[2,3-b]pyridine-2-carboxamide in 2 mL of chloroform is added dropwise 0.31 mL of a 0.7M solution of meta-chloroperbenzoic acid in chloroform. The solution is stirred at 0° C. for 4 hours and then at room temperature for 16 hours. The reaction mixture is diluted with 3 mL of dichloromethane and filtered through a No. 4 sinter funnel, and the solid obtained is washed twice with 3 mL of dichloromethane and then dried in air. 40 mg of 3-{4-[3-(2-fluoro-5-trifluoromethylphenyl)ureido]phenyl}-7-oxy-1H-pyrrolo[2,3-b]pyridine-2-carboxamide are obtained in the form of a pale yellow solid, the characteristics of which are as follows:

IR (KBr): 3352; 1671; 1609; 1545; 1442; 1340; 1315; 1239; 1119; 1069 and 885 cm$^{-1}$ $^1$H NMR: 7.16 (m, 1H); from 7.35 to 7.58 (m, 7H); 7.63 (broad m, 1H); 7.77 (broad m, 1H); 8.31 (broad d, J=6.0 Hz, 1H); 8.65 (broad d, J=8.5 Hz, 1H); 8.94 (broad s, 1H); 9.29 (s, 1H); from 12.5 to 13.2 (very broad m, 1H).

Mass spectrum (ES$^+$): m/z=474 [M+H$^+$]

Melting point: 220° C. (Köfler).

EXAMPLE 9

3-{4-[3-(2-Fluorophenyl)ureido]phenyl}-1H-pyrrolo[2,3-b]-pyridine-2-carboxamide

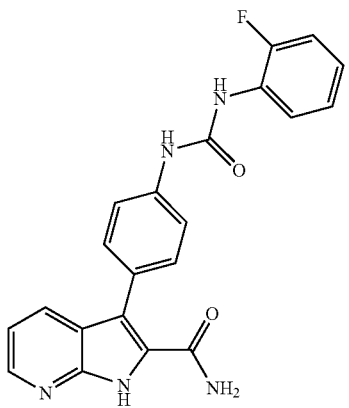

66.6 mg of solid beige-coloured 3-{4-[3-(2-fluorophenyl)ureido]phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 2-fluorophenyl isocyanate.
  Melting point=268.7° C. (Büchi)
  Mass spectrum (ES$^+$): [M+H]$^+$=390
  Retention time (min): 3.71

EXAMPLE 10

3-{4-[3-(2-Methoxyphenyl)ureido]phenyl}-1H-pyrrolo[2,3-b]-pyridine-2-carboxamide

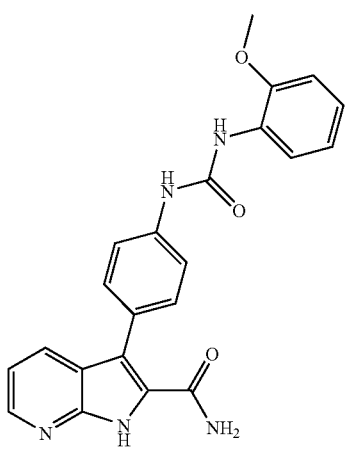

83.6 mg of solid beige-coloured 3-{4-[3-(2-methoxyphenyl)ureido]phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 2-methoxyphenyl isocyanate.
  Melting point: 227.1° C. (Büchi)
  Mass spectrum (ES$^+$): [M+H]$^+$=402
  Retention time (min): 3.77

EXAMPLE 11

3-{4-[3-(4-Trifluoromethylphenyl)ureido]phenyl}-1H-pyrrolo-[2,3-b]pyridine-2-carboxamide

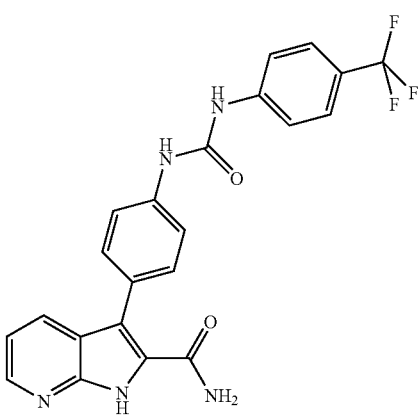

77.6 mg of solid white 3-{4-[3-(4-trifluoromethylphenyl)ureido]phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 4-trifluoromethylphenyl isocyanate.
  Melting point: 296.2° C. (Büchi)
  Mass spectrum (ES$^+$): [M+H]$^+$=440
  Retention time (min): 4.24

EXAMPLE 12

3-{4-[3-(2-Chloro-5-trifluoromethylphenyl)ureido]phenyl}-1H-pyrrolo[2,3-b]pyridine-2-carboxamide

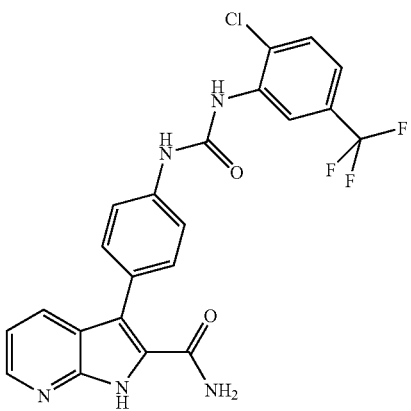

40.56 mg of solid white 3-{4-[3-(2-chloro-5-trifluoromethylphenyl)ureido]-phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 2-chloro-5-trifluoromethylphenyl isocyanate.
  Melting point: 188.3° C. (Büchi)
  Mass spectrum (ES$^+$): [M+H]$^+$=474
  Retention time (min): 4.51

EXAMPLE 13

3-{4-[3-(2-Fluoro-3-trifluoromethylphenyl)ureido]phenyl}-1H-pyrrolo[2,3-b]pyridine-2-carboxamide

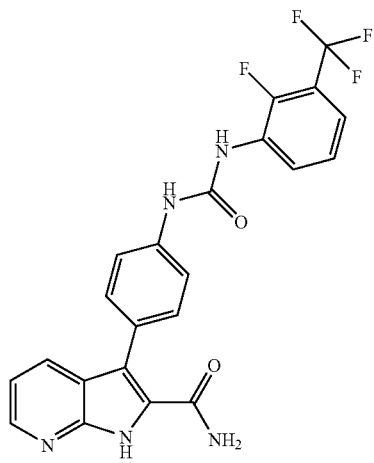

79 mg of solid white 3-{4-[3-(2-fluoro-3-trifluoromethylphenyl)ureido]phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 2-fluoro-3-trifluoromethylphenyl isocyanate.

Melting point: 265.4° C. (Büchi)
Mass spectrum (ES$^+$): [M+H]$^+$=458
Retention time (min): 4.24

EXAMPLE 14

3-{4-[3-(4-Fluoro-3-trifluoromethylphenyl)ureido]phenyl}-1H-pyrrolo[2,3-b]pyridine-2-carboxamide

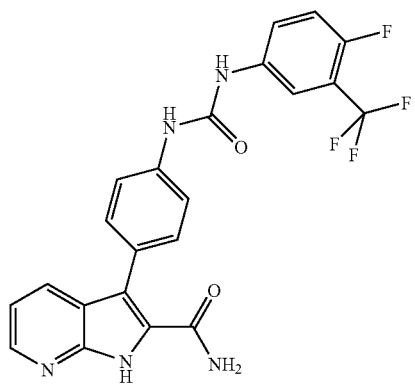

76.5 mg of solid brown 3-{4-[3-(4-fluoro-3-trifluoromethylphenyl)ureido]-phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 4-fluoro-3-trifluoromethylphenyl isocyanate.

Melting point: 234.7° C. (Büchi)
Mass spectrum (ES$^+$): [M+H]$^+$=458
Retention time (min): 4.22

EXAMPLE 15

3-{4-[3-(3-Fluoro-5-trifluoromethylphenyl)ureido]phenyl}-1H-pyrrolo[2,3-b]pyridine-2-carboxamide

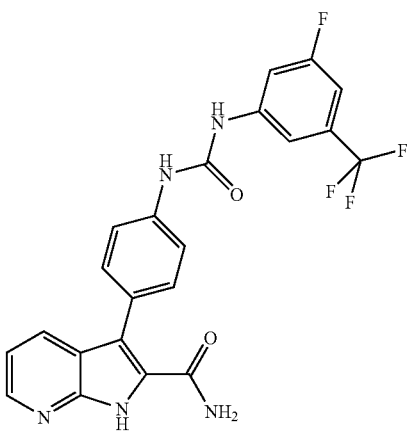

78.1 mg of solid beige-coloured 3-{4-[3-(3-fluoro-5-trifluoromethylphenyl)-ureido]phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 3-fluoro-5-trifluoromethylphenyl isocyanate.

Melting point: 257.5° C. (Büchi)
Mass spectrum (ES$^+$): [M+H]$^+$=458
Retention time (min): 4.42

EXAMPLE 16

3-{4-[3-(4-Trifluoromethoxyphenyl)ureido]phenyl}-1H-pyrrolo[2,3-b]pyridine-2-carboxamide

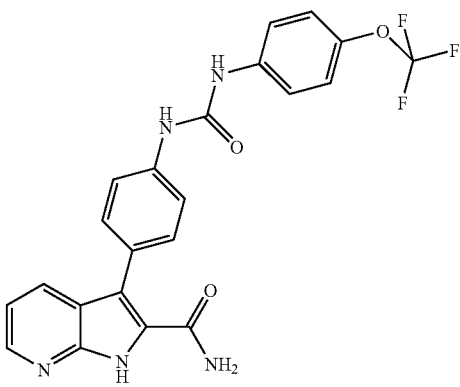

92.3 mg of brown powdered 3-{4-[3-(4-trifluoromethoxyphenyl)ureido]phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 4-trifluoromethoxyphenyl isocyanate.

Melting point: 258.9° C. (Büchi)
Mass spectrum (ES$^+$): [M+H]$^+$=456
Retention time (min): 4.29

EXAMPLE 17

3-{4-[3-(3,4-Dimethoxyphenyl)ureido]phenyl}-1H-pyrrolo-[2,3-b]pyridine-2-carboxamide

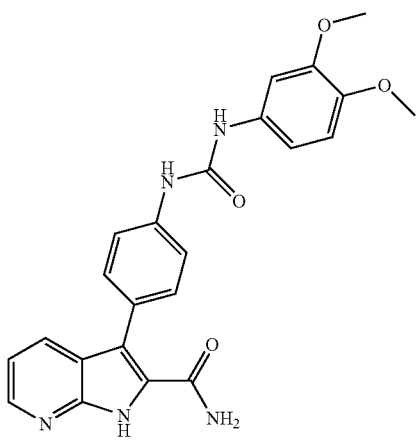

79 mg of solid beige-coloured 3-{4-[3-(3,4-dimethoxyphenyl)ureido]phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 3,4-dimethoxyphenyl isocyanate.

Melting point: 223.7° C. (Büchi)
Mass spectrum (ES$^+$): [M+H]$^+$=432
Retention time (min): 3.27

EXAMPLE 18

3-{4-[3-(2,5-Dimethylphenyl)ureido]phenyl}-1H-pyrrolo[2,3-b]pyridine-2-carboxamide

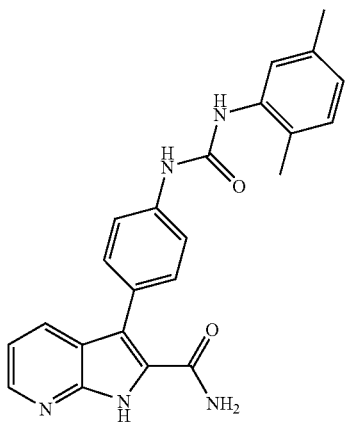

75.9 mg of solid white 3-{4-[3-(2,5-dimethylphenyl)ureido]phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 2,5-dimethylphenyl isocyanate.

Melting point: 308.8° C. (Büchi)
Mass spectrum (ES$^+$): [M+H]$^+$=400
Retention time (min): 3.90

EXAMPLE 19

3-{4-[3-(3-Methoxyphenyl)ureido]phenyl}-1H-pyrrolo[2,3-b]-pyridine-2-carboxamide

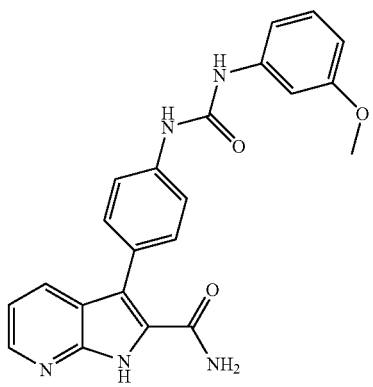

55.5 mg of solid beige-coloured 3-{4-[3-(3-methoxyphenyl)ureido]phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 3-methoxyphenyl isocyanate.

Melting point: 306.2° C. (Büchi)
Mass spectrum (ES$^+$): [M+H]$^+$=402
Retention time (min): 3.39

EXAMPLE 20

3-{4-[3-(3-Trifluoromethylphenyl)ureido]phenyl}-1H-pyrrolo-[2,3-b]-pyridine-2-carboxamide

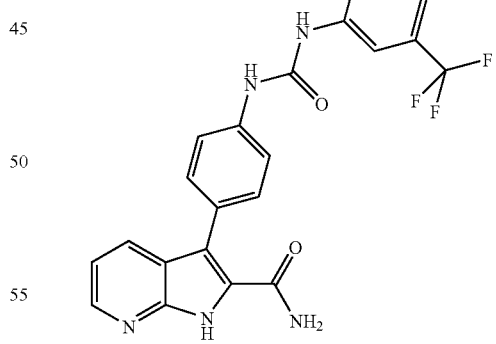

56.5 mg of solid white 3-{4-[3-(3-trifluoromethylphenyl)ureido]phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 3-trifluoromethylphenyl isocyanate.

Melting point: 263.6° C. (Büchi)
Mass spectrum (ES$^+$): [M+H]$^+$=440
Retention time (min): 3.95

EXAMPLE 21

3-{4-[3-(3,4-Dimethylphenyl)ureido]phenyl}-1H-pyrrolo[2,3-b]pyridine-2-carboxamide

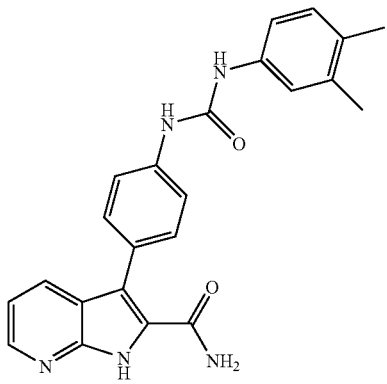

45.2 mg of solid white 3-{4-[3-(3,4-dimethylphenyl)ureido]phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 3,4-dimethylphenyl isocyanate.

Melting point: 274.7° C. (Büchi)
Mass spectrum (ES$^+$): [M+H]$^+$=400
Retention time (min): 3.75

EXAMPLE 22

3-{4-[3-(2-Methoxy-5-methylphenyl)ureido]phenyl}-1H-pyrrolo[2,3-b]pyridine-2-carboxamide

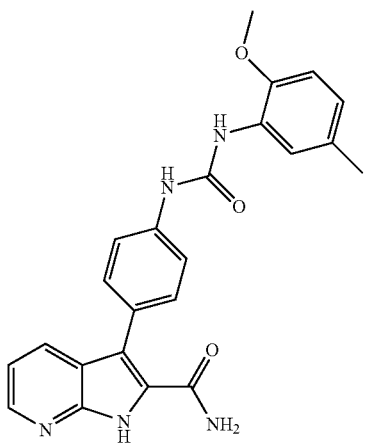

44.9 mg of solid beige-coloured 3-{4-[3-(2-methoxy-5-methylphenyl)ureido]-phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 2-methoxy-5-methylphenyl isocyanate.

Melting point: 327.7° C. (Büchi)
Mass spectrum (ES$^+$): [M+H]$^+$=416
Retention time (min): 3.76

EXAMPLE 23

3-[4-(3-m-Tolylureido)phenyl]-1H-pyrrolo[2,3-b]pyridine-2-carboxamide

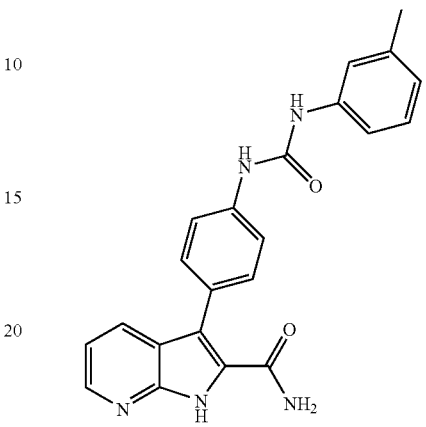

62.5 mg of solid beige-coloured 3-[4-(3-m-tolylureido)phenyl]-1H-pyrrolo[2,3-b]pyridine-2-carboxamide are prepared as described in Example 7 starting with 3-(4-aminophenyl)-1H-pyrrolo[2,3-b]pyridine-2-carboxamide and m-tolyl isocyanate.

Melting point: 266° C. (Büchi)
Mass spectrum (ES$^+$): [M+H]$^+$=386
Retention time (min): 3.60

EXAMPLE 24

3-{4-[3-(4-Fluorophenyl)ureido]phenyl}-1H-pyrrolo[2,3-b]-pyridine-2-carboxamide

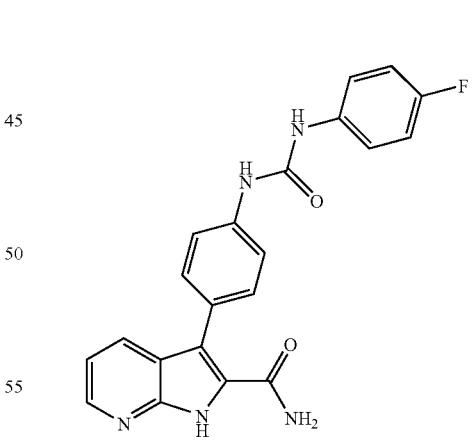

49.7 mg of solid beige-coloured 3-{4-[3-(4-fluorophenyl)ureido]phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 4-fluorophenyl isocyanate.

Melting point: 299.9° C. (Büchi)
Mass spectrum (ES$^+$): [M+H]$^+$=390
Retention time (min): 3.45

EXAMPLE 25

3-[4-(3-p-Tolylureido)phenyl]-1H-pyrrolo[2,3-b]pyridine-2-carboxamide

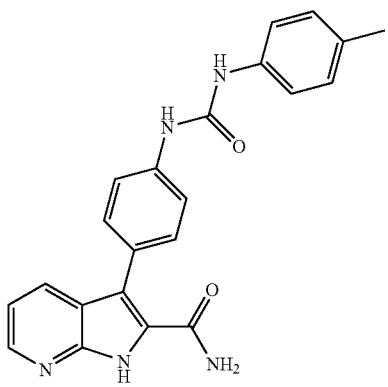

68.4 mg of solid beige-coloured 3-[4-(3-p-tolylureido)phenyl]-1H-pyrrolo[2,3-b]pyridine-2-carboxamide are prepared as described in Example 7 starting with 3-(4-aminophenyl)-1H-pyrrolo[2,3-b]pyridine-2-carboxamide and p-tolyl isocyanate.

Melting point: 293° C. (Büchi)

Mass spectrum (ES$^+$): [M+H]$^+$=386

Retention time (min): 3.58

EXAMPLE 26

3-{4-[3-(4-Methyl-3-trifluoromethylphenyl)ureido]phenyl}-1H-pyrrolo[2,3-b]pyridine-2-carboxamide

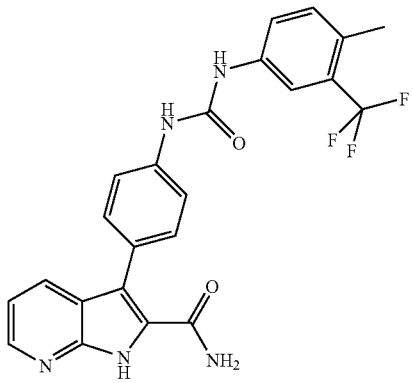

47.1 mg of solid white 3-{4-[3-(4-methyl-3-trifluoromethylphenyl)ureido]-phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 4-methyl-3-trifluoromethylphenyl isocyanate.

Melting point: 285° C.

Mass spectrum (ES$^+$): [M+H]$^+$=454

Retention time (min): 4.10

EXAMPLE 27

3-{4-[3-(4-Difluoromethoxyphenyl)ureido]phenyl}-1H-pyrrolo[2,3-b]pyridine-2-carboxamide

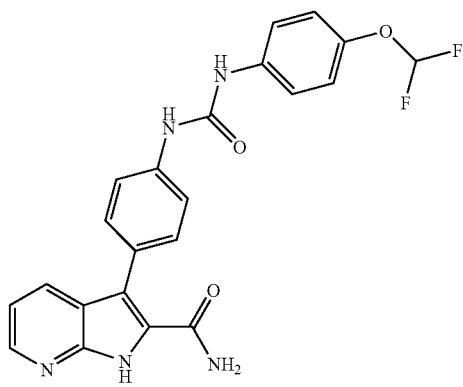

47.5 mg of solid white 3-{4-[3-(4-difluoromethoxyphenyl)ureido]phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 4-difluoromethoxyphenyl isocyanate.

Melting point: 283.5° C. (Büchi)

Mass spectrum (ES$^+$): [M+H]$^+$=438

Retention time (min): 3.64

EXAMPLE 28

3-{4-[3-(3,5-Dimethoxyphenyl)ureido]phenyl}-1H-pyrrolo-[2,3-b]pyridine-2-carboxamide

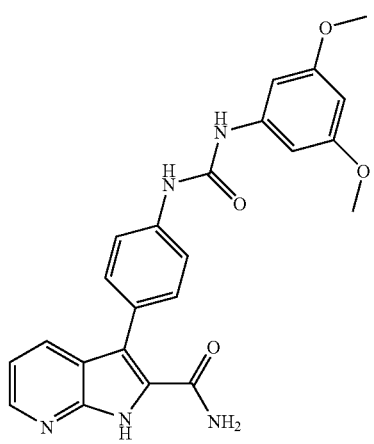

59.2 mg of solid beige-coloured 3-{4-[3-(3,5-dimethoxyphenyl)ureido]phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 3,5-dimethoxyphenyl isocyanate.

Melting point: 266.5° C. (Büchi)

Mass spectrum (ES$^+$): [M+H]$^+$=432

Retention time (min): 3.45

EXAMPLE 29

3-{4-[3-(4-Chloro-3-trifluoromethylphenyl)ureido]phenyl}-1H-pyrrolo[2,3-b]pyridine-2-carboxamide

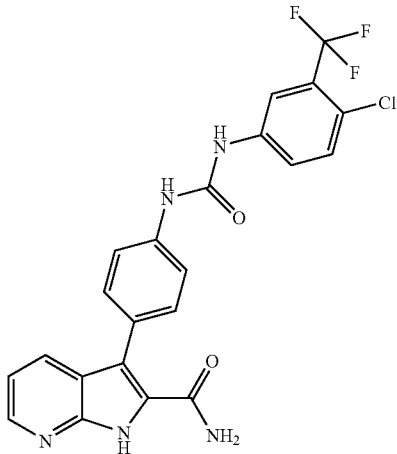

29.8 mg of solid white 3-{4-[3-(4-chloro-3-trifluoromethylphenyl)ureido]-phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 4-chloro-3-trifluoromethylphenyl isocyanate.
Melting point: 311.1° C. (Büchi)
Mass spectrum (ES+): [M+H]+=474
Retention time (min): 4.22

EXAMPLE 30

3-{4-[3-(2,5-Dimethoxyphenyl)ureido]phenyl}-1H-pyrrolo-[2,3-b]pyridine-2-carboxamide

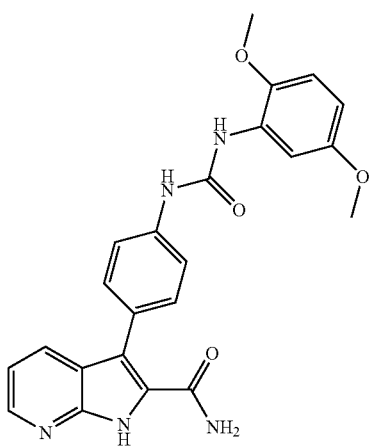

33.1 mg of yellow lyophilizate 3-{4-[3-(2,5-dimethoxyphenyl)ureido]phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 2,5-dimethoxyphenyl isocyanate.
Mass spectrum: LC-MS-DAD-ELSD: 432 (+)=(M+H)(+); 430 (−)=(M−H)(−)
Retention time (min): 3.53

EXAMPLE 31

3-{4-[3-(3-Fluorophenyl)ureido]phenyl}-1H-pyrrolo[2,3-b]-pyridine-2-carboxamide

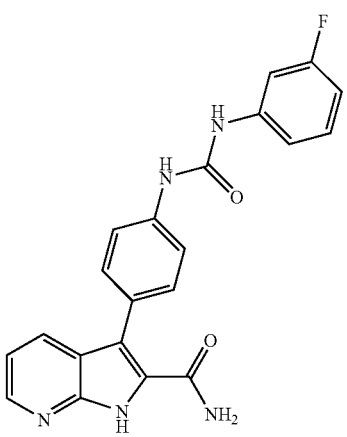

31.5 mg of white lyophilizate 3-{4-[3-(3-fluorophenyl)ureido]phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 3-fluorophenyl isocyanate.
Mass spectrum LC-MS-DAD-ELSD: 390(+)=(M+H)(+); 388(−)=(M−H)(−)
Retention time (min): 3.55

EXAMPLE 32

3-{4-[3-(2-Methoxy-5-trifluoromethylphenyl)ureido]phenyl}-1H-pyrrolo[2,3-b]pyridine-2-carboxamide

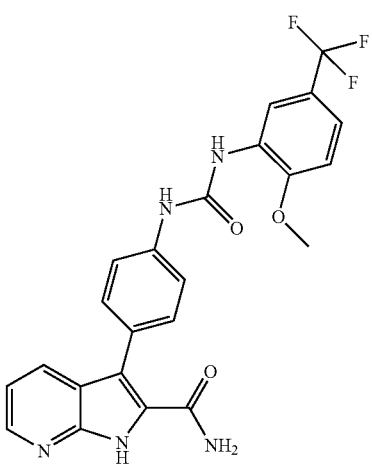

50 mg of solid beige-coloured 3-{4-[3-(2-methoxy-5-trifluoromethylphenyl)-ureido]phenyl}-1H-pyrrolo[2,3-b]pyridine-2-carboxamide are prepared as described in Example 7 starting with 3-(4-aminophenyl)-1H-pyrrolo[2,3-b]pyridine-2-carboxamide and 2-methoxy-5-trifluoromethylphenyl isocyanate.

Melting point: 221° C. (Köfler-sublimation)
Mass spectrum LC-MS-DAD-ELSD: 470(+)=(M+H)(+) 468(−)=(M−H)(−)

EXAMPLE 33

3-{4-[3-(2-Acetylamino-5-trifluoromethylphenyl)ureido]-phenyl}-1H-pyrrolo[2,3-c]pyridine-2-carboxamide trifluoroacetate

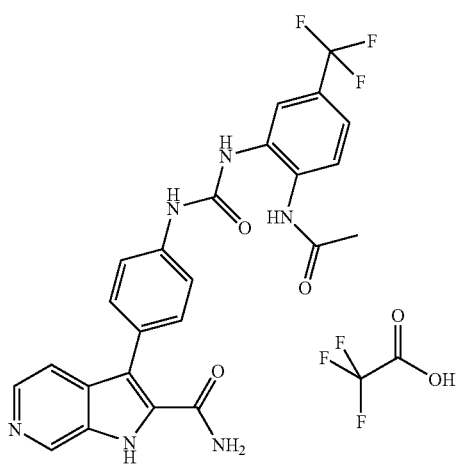

12 mg of solid yellow 3-{4-[3-(2-acetylamino-5-trifluoromethylphenyl)-ureido]phenyl}-1H-pyrrolo[2,3-c]pyridine-2-carboxamide trifluoroacetate are prepared as described in Example 1 starting with 3-(4-aminophenyl)-1H-pyrrolo[2,3-c]pyridine-2-carboxamide and 2-acetylamino-5-trifluoromethyl-phenyl isocyanate.

Mass spectrum (ES+): [M+H]+=497
Retention time (min): 2.63

EXAMPLE 34

3-{4-[3-(2-Methoxyphenyl)ureido]phenyl}-1H-pyrrolo[2,3-c]pyridine-2-carboxamide

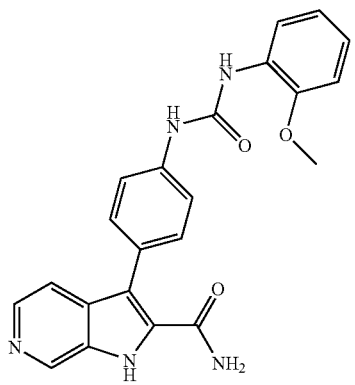

25 mg of solid yellow 3-{4-[3-(2-methoxyphenyl)ureido]phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 2-methoxyphenyl isocyanate.

Melting point: 216° C. (Köfler)
Mass spectrum (ES+): [M+H]+=402
Retention time (min): 3.06

EXAMPLE 35

3-{4-[3-(2-Trifluoromethylphenyl)ureido]phenyl}-1H-pyrrolo[2,3-c]pyridine-2-carboxamide

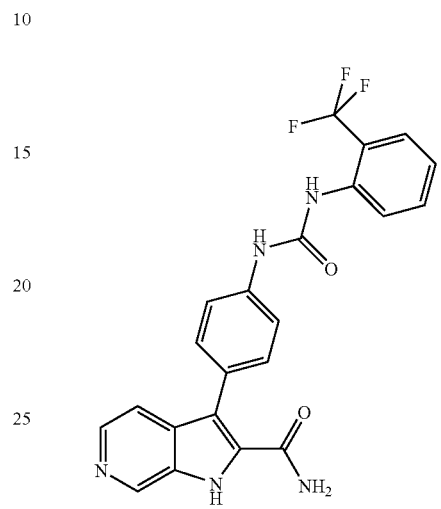

80 mg of solid yellow 3-{4-[3-(2-trifluoromethylphenyl)ureido]phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 2-trifluoromethylphenyl isocyanate.

Melting point: 228° C. (Köfler)
Mass spectrum (ES+): [M+H]+=440
Retention time (min): 3.17

EXAMPLE 36

3-{4-[3-(3-Trifluoromethylphenyl)ureido]phenyl}-1H-pyrrolo-[2,3-c]pyridine-2-carboxamide

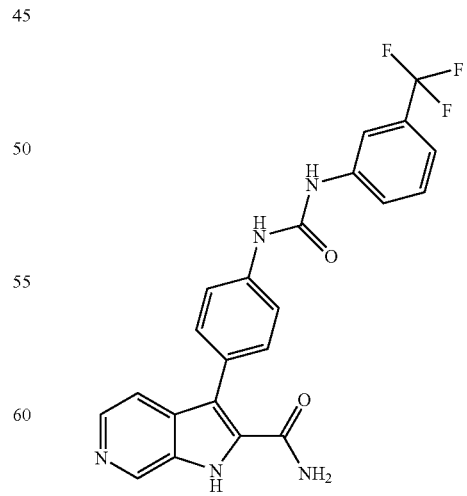

77 mg of solid yellow 3-{4-[3-(3-trifluoromethylphenyl)ureido]phenyl}-1H-pyrrolo[2,3-c]pyridine-2-carboxamide are prepared as described in Example 1 starting with 3-(4- aminophenyl)-1H-pyrrolo[2,3-c]pyridine-2-carboxamide and 3-trifluoromethylphenyl isocyanate.
Melting point: 256° C. (Büchi B-545)
Mass spectrum (ES⁺): [M+H]⁺=440
Retention time (min): 3.48

EXAMPLE 37

3-{4-[3-(4-Fluorophenyl)ureido]phenyl}-1H-pyrrolo[2,3-c]-pyridine-2-carboxamide

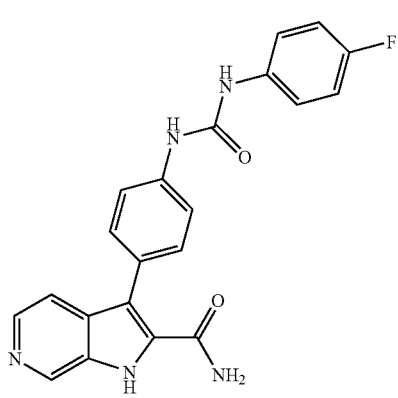

73 mg of solid yellow 3-{4-[3-(4-fluorophenyl)ureido]phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 4-fluorophenyl isocyanate.
Melting point: 271° C. (Büchi B-545)
Mass spectrum (ES⁺): [M+H]⁺=390
Retention time (min): 2.93

EXAMPLE 38

3-{4-[3-(4-Trifluoromethylphenyl)ureido]phenyl}-1H-pyrrolo-[2,3-c]pyridine-2-carboxamide

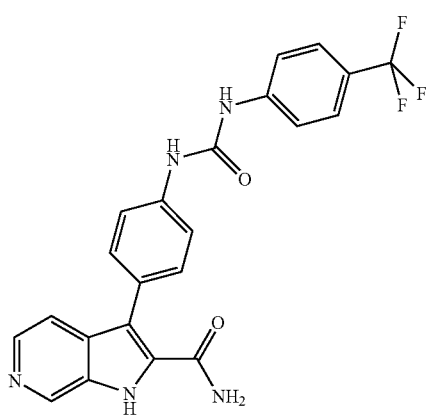

91 mg of solid yellow 3-{4-[3-(4-trifluoromethylphenyl)ureido]phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 4-trifluoromethylphenyl isocyanate.
Melting point: 289° C.
Mass spectrum (ES⁺): [M+H]⁺=440
Retention time (min): 3.48

EXAMPLE 39

3-[4-(3-p-Tolylureido)phenyl]-1H-pyrrolo[2,3-c]pyridine-2-carboxamide

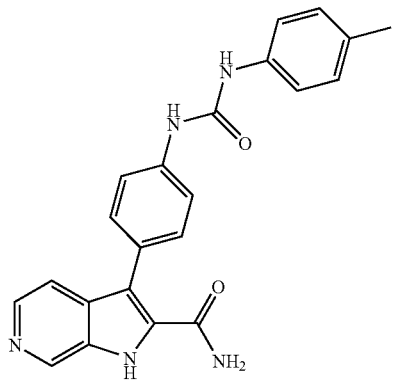

76 mg of solid yellow 3-[4-(3-p-tolylureido)phenyl]-1H-pyrrolo[2,3-c]pyridine-2-carboxamide are prepared as described in Example 1 starting with 3-(4-aminophenyl)-1H-pyrrolo[2,3-c]pyridine-2-carboxamide and p-tolyl isocyanate.
Melting point: 277° C. (Büchi B-545)
Mass spectrum (ES⁺): [M+H]⁺=386
Retention time (min): 3.13

EXAMPLE 40

3-{4-[3-(4-Chloro-3-trifluoromethylphenyl)ureido]phenyl}-1H-pyrrolo[2,3-c]pyridine-2-carboxamide

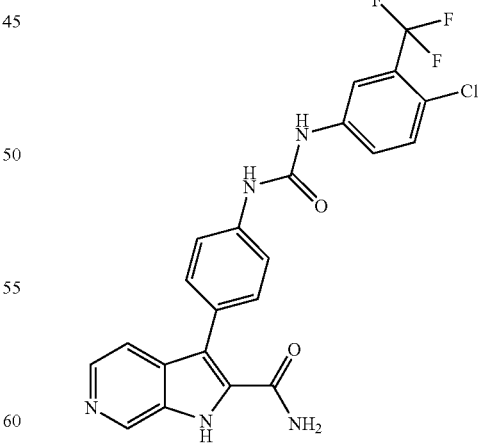

103 mg of solid yellow 3-{4-[3-(4-chloro-3-trifluoromethylphenyl)ureido]-phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 4-chloro-3-trifluoromethylphenyl isocyanate.

Melting point: 228° C. (Büchi B-545)
Mass spectrum (ES+): [M+H]+=474
Retention time (min): 3.64

EXAMPLE 41

3-{4-[3-(2-Chloro-5-trifluoromethylphenyl)ureido]phenyl}-1H-pyrrolo[2,3-c]pyridine-2-carboxamide

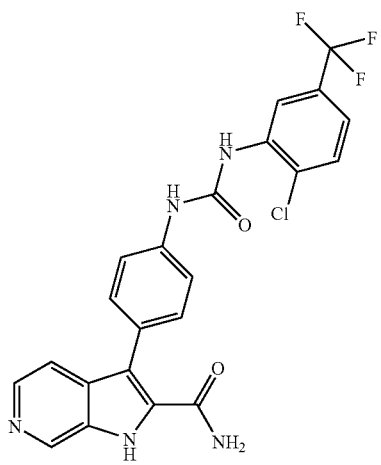

76 mg of solid yellow 3-{4-[3-(2-chloro-5-trifluoromethylphenyl)ureido]phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 2-chloro-5-trifluoromethylphenyl isocyanate.
Melting point: 243° C. (Büchi B-545)
Mass spectrum (ES+): [M+H]+=474
Retention time (min): 3.56

EXAMPLE 42

3-{4-[3-(4-Trifluoromethoxyphenyl)ureido]phenyl}-1H-pyrrolo[2,3-c]pyridine-2-carboxamide

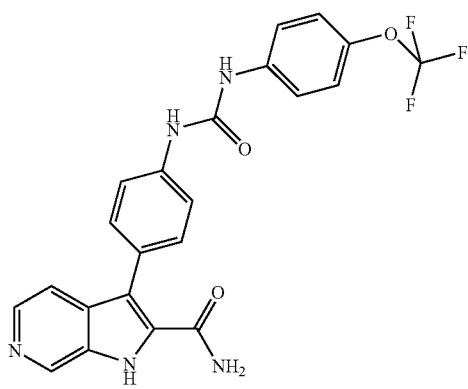

94 mg of solid yellow 3-{4-[3-(4-trifluoromethoxyphenyl)ureido]phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 4-trifluoromethoxyphenyl isocyanate.

Melting point: 276° C. (Büchi B-545)
Mass spectrum (ES+): [M+H]+=456
Retention time (min): 3.63

EXAMPLE 43

3-{4-[3-(4-Difluoromethoxyphenyl)ureido]phenyl}-1H-pyrrolo[2,3-c]pyridine-2-carboxamide

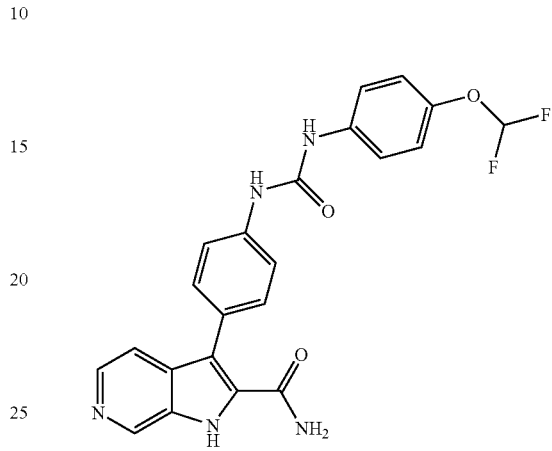

87 mg of solid yellow 3-{4-[3-(4-difluoromethoxyphenyl)ureido]phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 4-difluoromethoxyphenyl isocyanate.
Melting point: 257° C.
Mass spectrum (ES+): [M+H]+=438
Retention time (min): 3.23

EXAMPLE 44

3-{4-[3-(3,4-Dimethylphenyl)ureido]phenyl}-1H-pyrrolo[2,3-c]pyridine-2-carboxamide

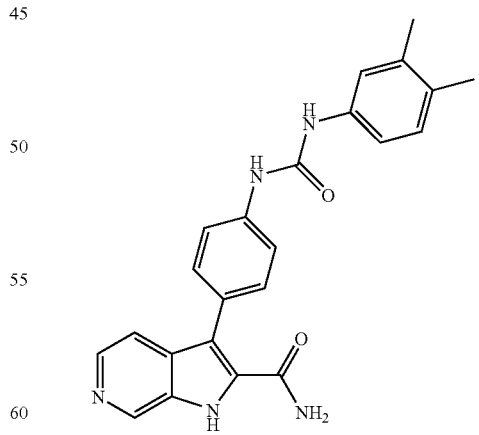

82 mg of solid yellow 3-{4-[3-(3,4-dimethylphenyl)ureido]phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 3,4-dimethylphenyl isocyanate.

EXAMPLE 45

3-{4-[3-(3,5-Dimethoxyphenyl)ureido]phenyl}-1H-pyrrolo-[2,3-c]pyridine-2-carboxamide

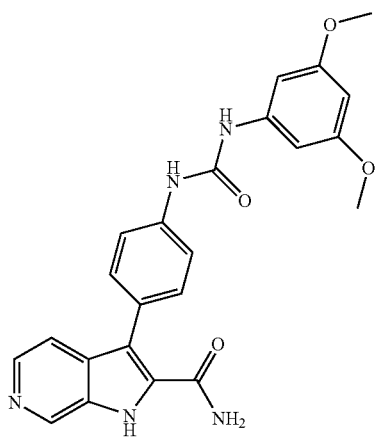

87 mg of solid yellow 3-{4-[3-(3,5-dimethoxyphenyl)ureido]phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 3,5-dimethoxyphenyl isocyanate.

Melting point: 225° C. (Büchi B-545)
Mass spectrum (ES$^+$): [M+H]$^+$=432
Retention time (min): 3.07

EXAMPLE 46

3-{4-[3-(2,5-Dimethylphenyl)ureido]phenyl}-1H-pyrrolo[2,3-c]pyridine-2-carboxamide

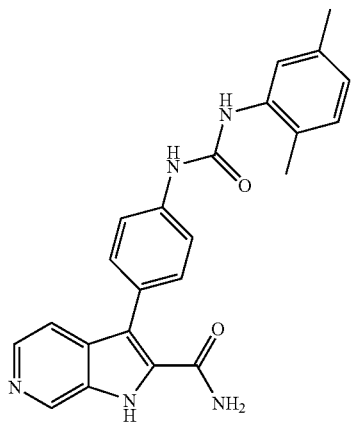

87 mg of solid yellow 3-{4-[3-(2,5-dimethylphenyl)ureido]phenyl}-1H-pyrrolo-[2,3-c]pyridine-2-carboxamide are prepared as described in Example 1 starting with 3-(4-aminophenyl)-1H-pyrrolo[2,3-c]pyridine-2-carboxamide and 2,5-dimethylphenyl isocyanate.

EXAMPLE 47

3-{4-[3-(2-Fluorophenyl)ureido]phenyl}-1H-pyrrolo[2,3-c]-pyridine-2-carboxamide

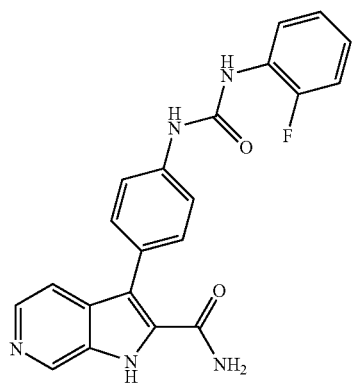

59 mg of pale yellow solid 3-{4-[3-(2-fluorophenyl)ureido]phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 2-fluorophenyl isocyanate.

Melting point: 242° C. (Büchi B-545)
Mass spectrum (ES$^+$): [M+H]$^+$=390
Retention time (min): 2.41

EXAMPLE 48

3-{4-[3-(3-Fluorophenyl)ureido]phenyl}-1H-pyrrolo[2,3-c]-pyridine-2-carboxamide

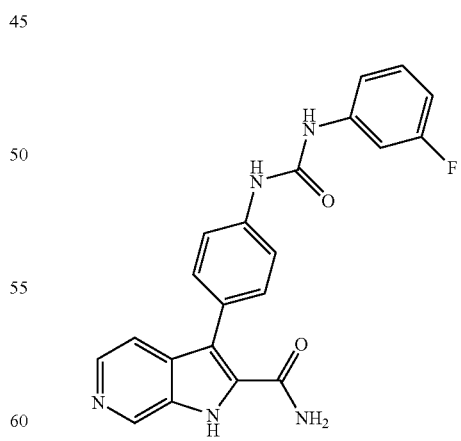

63 mg of pale yellow solid 3-{4-[3-(3-fluorophenyl)ureido]phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 3-fluorophenyl isocyanate.

EXAMPLE 49

3-{4-[3-(2-Fluoro-3-trifluoromethylphenyl)ureido]phenyl}-1H-pyrrolo[2,3-c]pyridine-2-carboxamide

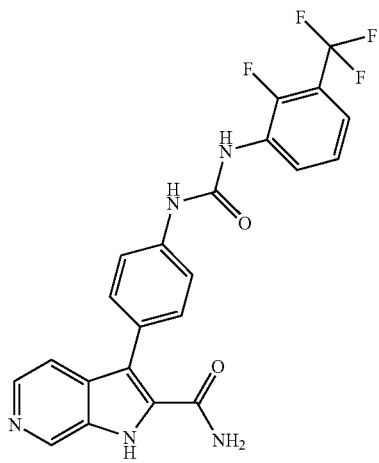

69 mg of pale yellow solid 3-{4-[3-(2-fluoro-3-trifluoromethylphenyl)ureido]phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 2-fluoro-3-trifluoromethylphenyl isocyanate.
Melting point: 240° C. (Büchi B-545)
Mass spectrum (ES+): [M+H]+=458
Retention time (min): 2.75

EXAMPLE 50

3-{4-[3-(3-Fluoro-5-trifluoromethylphenyl)ureido]phenyl}-1H-pyrrolo[2,3-c]pyridine-2-carboxamide

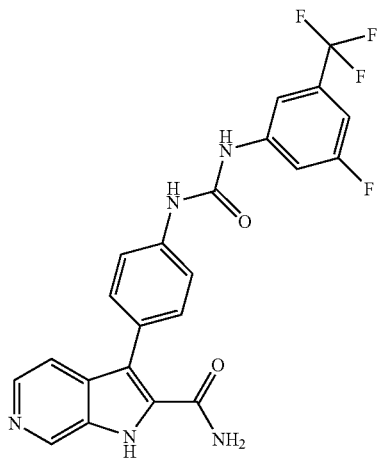

69 mg of pale yellow solid 3-{4-[3-(3-fluoro-5-trifluoromethylphenyl)ureido]-phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 3-fluoro-5-trifluoromethylphenyl isocyanate.
Melting point: 252° C. (Büchi B-545)
Mass spectrum (ES+): [M+H]+=390
Retention time (min): 2.55

EXAMPLE 51

3-{4-[3-(4-Fluoro-3-trifluoromethylphenyl)ureido]phenyl}-1H-pyrrolo[2,3-c]pyridine-2-carboxamide

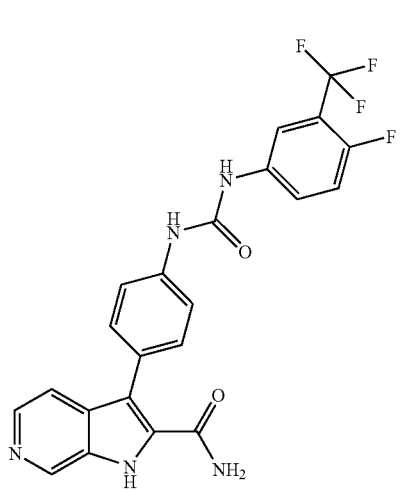

56 mg of pale yellow solid 3-{4-[3-(4-fluoro-3-trifluoromethylphenyl)ureido]-phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 4-fluoro-3-trifluoromethylphenyl isocyanate.
Melting point: 201° C. (Büchi B-545)
Mass spectrum (ES+): [M+H]+=458
Retention time (min): 2.85

EXAMPLE 52

3-{4-[3-(4-Methyl-3-trifluoromethylphenyl)ureido]phenyl}-1H-pyrrolo[2,3-c]pyridine-2-carboxamide

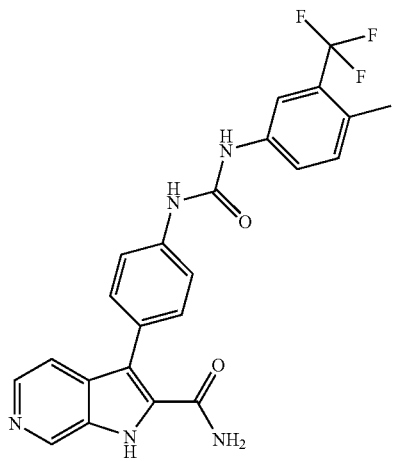

61 mg of pale yellow solid 3-{4-[3-(4-methyl-3-trifluoromethylphenyl)ureido]-phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 4-methyl-3-trifluoromethylphenyl isocyanate.

Melting point: 199° C.
Mass spectrum (ES+): [M+H]+=454
Retention time (min): 2.84

EXAMPLE 53

3-{4-[3-(3-Methoxyphenyl)ureido]phenyl}-1H-pyrrolo[2,3-c]-pyridine-2-carboxamide trifluoroacetate

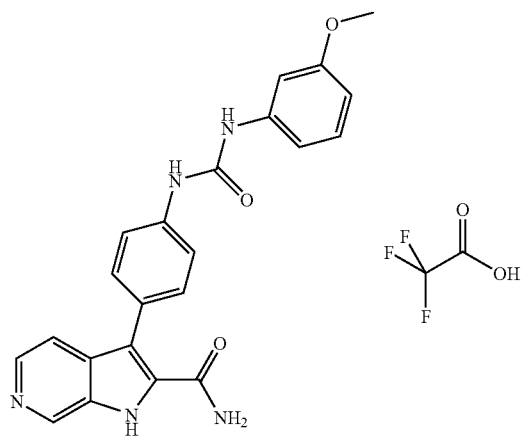

33.3 mg of yellow lyophilizate 3-{4-[3-(3-methoxyphenyl)ureido]phenyl}-1H-pyrrolo[2,3-c]pyridine-2-carboxamide trifluoroacetate are prepared as described in Example 1 starting with 3-(4-aminophenyl)-1H-pyrrolo[2,3-c]pyridine-2-carboxamide and 3-methoxyphenyl isocyanate.

Mass spectrum (ES+): [M+H]+=402
Retention time (min): 2.60

EXAMPLE 54

3-{4-[3-(3,4-Dimethoxyphenyl)ureido]phenyl}-1H-pyrrolo-[2,3-c]pyridine-2-carboxamide trifluoroacetate

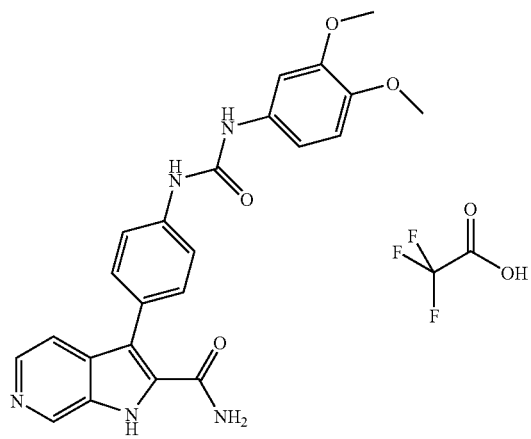

80.5 mg of yellow lyophilizate 3-{4-[3-(3,4-dimethoxyphenyl)ureido]phenyl}-1H-pyrrolo[2,3-c]pyridine-2-carboxamide trifluoroacetate are prepared as described in Example 1 starting with 3-(4-aminophenyl)-1H-pyrrolo[2,3-c]pyridine-2-carboxamide and 3,4-dimethoxyphenyl isocyanate.

Mass spectrum (ES+): [M+H]+=432
Retention time (min): 2.27

EXAMPLE 55

3-{4-[3-(2,5-Dimethoxyphenyl)ureido]phenyl}-1H-pyrrolo-[2,3-c]pyridine-2-carboxamide trifluoroacetate

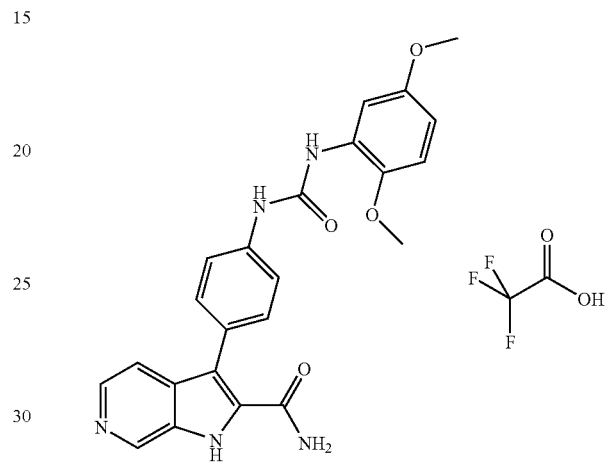

90.7 mg of yellow lyophilizate 3-{4-[3-(2,5-dimethoxyphenyl)ureido]phenyl}-1H-pyrrolo[2,3-c]pyridine-2-carboxamide trifluoroacetate are prepared as described in Example 1 starting with 3-(4-aminophenyl)-1H-pyrrolo[2,3-c]pyridine-2-carboxamide and 2,5-dimethoxyphenyl isocyanate.

Mass spectrum (ES+): [M+H]+=432
Retention time (min): 2.62

EXAMPLE 56

3-[4-(3-o-Tolylureido)phenyl]-1H-pyrrolo[2,3-c]pyridine-2-carboxamide

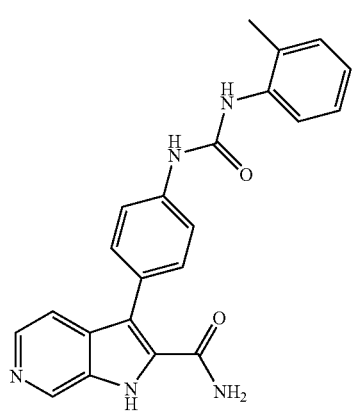

75.3 mg of pale yellow solid 3-[4-(3-o-tolylureido)phenyl]-1H-pyrrolo[2,3-c]-pyridine-2-carboxamide are prepared as described in Example 1 starting with 3-(4-aminophenyl)-1H-pyrrolo[2,3-c]pyridine-2-carboxamide and O-tolyl isocyanate.

Melting point: 270° C. (Büchi B-545)
Mass spectrum (ES+): [M+H]+=386
Retention time (min): 2.54

EXAMPLE 57

3-{4-[3-(4-Methoxyphenyl)ureido]phenyl}-1H-pyrrolo[2,3-c]pyridine-2-carboxamide

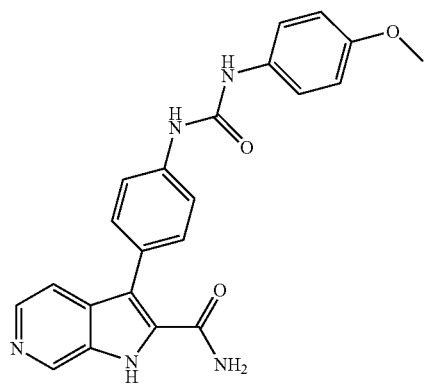

51.1 mg of pale yellow solid 3-{4-[3-(4-methoxyphenyl)ureido]phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 4-methoxyphenyl isocyanate.

Melting point: 275° C. (Büchi B-545)
Mass spectrum (ES+): [M+H]+=402
Retention time (min): 2.28

EXAMPLE 58

3-{4-[3-(3-Chloro-4-difluoromethoxyphenyl)ureido]phenyl}-1H-pyrrolo[2,3-c]pyridine-2-carboxamide

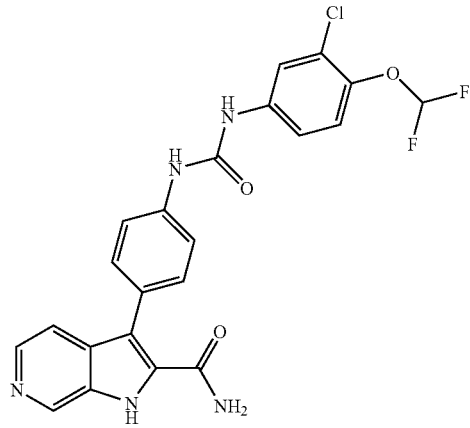

93 mg of pale yellow solid 3-{4-[3-(3-chloro-4-difluoromethoxyphenyl)-ureido]phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 3-chloro-4-difluoromethoxyphenyl isocyanate.

Melting point: 267° C. (Büchi B-545)
Mass spectrum (ES+): [M+H]+=472
Retention time (min): 2.90

EXAMPLE 59

3-{4-[3-(3,5-Dimethylphenyl)ureido]phenyl}-1H-pyrrolo[2,3-c]pyridine-2-carboxamide

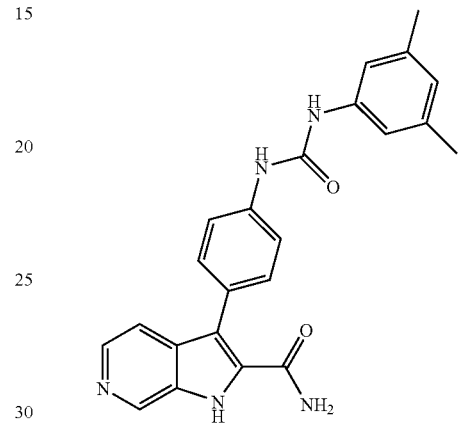

61 mg of pale yellow solid 3-{4-[3-(3,5-dimethylphenyl)ureido]phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 3,5-dimethylphenyl isocyanate.

Melting point: 188° C. (Büchi B-545)
Mass spectrum (ES+): [M+H]+=400
Retention time (min): 2.68

EXAMPLE 60

3-{4-[3-(3-Ethylphenyl)ureido]phenyl}-1H-pyrrolo[2,3-c]-pyridine-2-carboxamide

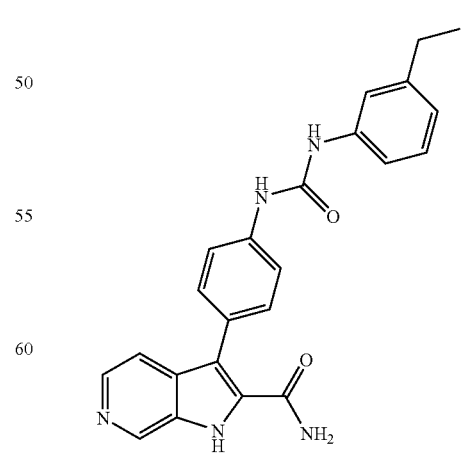

61 mg of pale yellow solid 3-{4-[3-(3-ethylphenyl)ureido]phenyl}-1H-pyrrolo[2,3-c]pyridine-2-carboxamide are prepared as described in Example 1 starting with 3-(4-aminophenyl)-1H-pyrrolo[2,3-c]pyridine-2-carboxamide and 3-ethylphenyl isocyanate.

Melting point: 257° C. (Büchi B-545)
Mass spectrum (ES+): [M+H]+=400
Retention time (min): 2.97

EXAMPLE 61

3-{4-[3-(3-Ethylphenyl)ureido]phenyl}-1H-pyrrolo[2,3-b]-pyridine-2-carboxamide

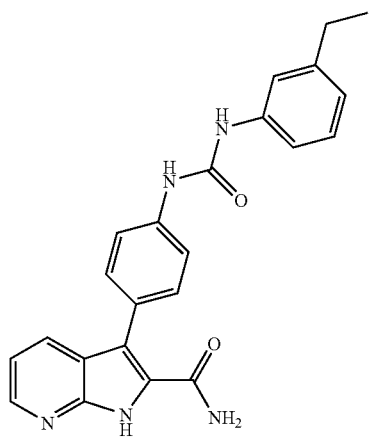

0.8 mg of solid white 3-{4-[3-(3-ethylphenyl)ureido]phenyl}-1H-pyrrolo[2,3-b]pyridine-2-carboxamide is prepared as described in Example 7 starting with 3-(4-aminophenyl)-1H-pyrrolo[2,3-b]pyridine-2-carboxamide and 3-ethylphenyl isocyanate.

Melting point: 254° C. (Büchi)
Mass spectrum (ES+): [M+H]+=400
Retention time (min): 7.18

Determination of the Activity of the Compounds—Experimental Protocols

1. FAK

The inhibitory activity of the compounds on FAK is determined by measuring the inhibition of autophosphorylation of the enzyme using a time-resolved fluorescence test (HTRF).

The whole cDNA of human FAK, the N-terminal end of which has been labelled with histidine, was cloned in a pFastBac HTc baculovirus expression vector. The protein was expressed and purified to about 70% homogeneity.

The kinase activity is determined by incubating the enzyme (6.6 μg/ml) with different concentrations of test compound in a 50 mM Hepes pH=7.2, 10 mM MgCl$_2$, 100 μm Na$_3$VO$_4$, 15 μM ATP buffer for 1 hour at 37° C. The enzymatic reaction is stopped by adding Hepes pH=7.0 buffer containing 0.4 mM KF, 133 mM EDTA, 0.1% BSA and the labelling is performed, for 1 to 2 hours at room temperature, by adding to this buffer an anti-Histidine antibody labelled with XL665 and a tyrosine phosphospecific monoclonal antibody conjugated to europium cryptate (Eu—K). The characteristics of the two fluorophores are available in G. Mathis et al., Anticancer Research, 1997, 17, pages 3011-3014. The energy transfer from the excited europium cryptate to the acceptor XL665 is proportional to the degree of autophosphorylation of FAK. The long-lasting signal specific for XL-665 is measured in a Packard Discovery plate counter. All the tests are performed in duplicate and the average of the two tests is calculated. The inhibition of the autophosphorylation activity of FAK with compounds of the invention is expressed as a percentage of inhibition relative to a control whose activity is measured in the absence of test compound. To calculate the percentage inhibition, the ratio [signal at 665 nm/signal at 620 nm] is considered.

2. KDR

The inhibitory effect of the compounds is determined in an in vitro test of phosphorylation of substrate with the enzyme KDR via a scintillation technique (96-well plate, NEN).

The cytoplasmic domain of the human KDR enzyme was cloned in the form of a GST fusion in the pFastBac baculovirus expression vector. The protein was expressed in the SF21 cells and purified to about 60% homogeneity.

The KDR kinase activity is measured in 20 mM MOPS, 10 mM MgCl$_2$, 10 mM MnCl$_2$, 1 mM DTT, 2.5 mM EGTA, 10 mM b-glycerophosphate, pH=7.2, in the presence of 10 mM MgCl$_2$, 100 μm Na$_3$VO$_4$, 1 mM NaF. 10 μl of the compound are added to 70 μl of kinase buffer containing 100 ng of KDR enzyme at 4° C. The reaction is initiated by adding 20 μl of solution containing 2 μg of substrate (SH2-SH3 fragment of PLCγ expressed in the form of a GST fusion protein), 2 μCi of γ$^{33}$P[ATP] and 2 μm of cold ATP. After incubation for 1 hour at 37° C., the reaction is stopped by adding 1 volume (100 μl) of 200 mM EDTA. The incubation buffer is removed, and the wells are washed three times with 300 μl of PBS. The radioactivity in each well is measured using a Top Count NXT radioactivity counter (Packard).

The background noise is determined by measuring the radioactivity in four different wells containing radioactive ATP and the substrate alone.

A total activity control is measured in four different wells containing all the reagents (γ$^{33}$P-[ATP], KDR and substrate PLCγ), but in the absence of compound.

The inhibition of the KDR activity with the compound of the invention is expressed as a percentage of inhibition of the control activity determined in the absence of compound.

Compound SU5614 (Calbiochem) (1 μM) is included in each plate as an inhibition control.

3. Tie2

The coding sequence of human Tie2 corresponding to the amino acids of the intracellular domain 776-1124 was generated by PCR using the cDNA isolated from a human placenta as a model. This sequence was introduced into a pFastBacGT baculovirus expression vector in the form of a GST fusion protein.

The inhibitory effect of the molecules is determined in a test of phosphorylation of PLC with Tie2 in the presence of GST-Tie2 purified to about 80% homogeneity. The substrate is composed of the SH2-SH3 fragments of PLC expressed in the form of a GST fusion protein.

The kinase activity of Tie2 is measured in a MOPS 20 mM pH 7.2 buffer, containing 10 mM MgCl$_2$, 10 mM MnCl$_2$, 1 mM DTT, 10 mM of glycerophosphate. In a 96-well FlashPlate plate maintained on ice, a reaction mixture is deposited, composed of 70 μL of kinase buffer containing 100 ng of enzyme GST-Tie2 per well. Next, 10 μL of the test molecule diluted in DMSO to a maximum concentration of 10% are added. For a given concentration, each measurement is performed four times. The reaction is initiated by adding 20 μl of solution containing 2 μg of GST-PLC, 2 μm of cold ATP and 1 μCi of $^{33}$P[ATP]. After incubation for one hour at 37° C., the reaction is stopped by adding 1 volume (100 μl) of 200 mM EDTA. After removal of the incubation buffer, the wells are washed three times with 300 μL of PBS. The radioactivity is measured on a MicroBeta 1450 Wallac.

The inhibition of the Tie2 activity is calculated and expressed as a percentage of inhibition relative to the control activity determined in the absence of compound.

4. Aurora1 and Aurora2

The inhibitory effect of compounds with respect to the kinases Aurora1 and Aurora2 is determined by means of an enzymatic test using radioactivity detection.

The kinase activity of Aurora1 and Aurora2 is evaluated via the phosphorylation of the substrate Numa-histidine in the presence of radiolabelled ATP ([$^{33}$P]ATP) using 96-well Flashplate plates in which the nickel chelate is bound to the surface of the microplate. The amount of $^{33}$P phosphate incorporated into the NuMA substrate is proportional to the activity of the enzyme Aurora1 or Aurora2.

Proteins:

The proteins are produced in the protein production laboratory of the Sanofi-Aventis group.

Aurora1: Aurora-B/INCENP-C3 recombinant complex, purified to about 50%, the N-terminal end of Aurora-B of which has been labelled with histidine.

Aurora2: whole recombinant protein comprising an N-terminal histidine tail, was expressed in *E. coli* and purified to more than 82%.

NuMA (nuclear protein that combines with the mitotic apparatus): 424-amino acid fragment, expressed in *E. coli*, the N-terminal end of which has been labelled with histidine, and used as substrate for the two Aurora enzymes.

Protocol:

The microplates used are 96-well Flash-Plate plates, nickel chelate (Perkin-Elmer, model SMP107).

The products to be evaluated are incubated in a reaction volume of 100 µL per well, in the presence of 10 nM of Aurora1 or Aurora2, 500 nM of NuMA substrate in a buffer composed of 50 mM Tris/HCl (pH 7.5), 50 mM NaCl, 5 mM MgCl$_2$ (Aurora-B) or 10 mM MgCl$_2$ (Aurora-A) and 1 mM DTT, at 37° C.

80 µL of enzyme/substrate incubation buffer are distributed in each well, followed by 10 µL of product to be evaluated, at variable concentrations. The reaction is initiated by adding 1 µM final of ATP containing 0.2 µCi of [$^{33}$P]ATP (10 µL). After incubating for 30 minutes, the reaction is quenched by simple removal of the reaction buffer and each well is washed twice with 300 µl of Tris/HCl buffer. The radioactivity is then measured in each well using a Packard, Top-Count model scintillation machine.

The control enzymatic activity of Aurora is expressed by the number of counts per minute obtained over 30 minutes after subtracting the background noise (reaction mixture containing no enzyme). The evaluation of the various test products is expressed as a percentage of inhibition of the Aurora activity relative to the control.

5. CDK2/cycline E:

Purification of the CDK2/cyclineE-(His)$_6$ Complex by IMAC (Immobilized Metal Affinity Chromatography):

Two recombinant baculoviruses bearing the human sequences coding, respectively, for CDK2 and cyclineE (the latter bearing a C-terminal hexahistidine tag) are used to coinfect Sf21 insect cells. Two to three days after the start of coinfection, the cells are harvested by centrifugation and then stored at −40° C. until the time of use. After thawing and mechanical lysis of the cells, the complex present in the lysis supernatant is purified by affinity chromatography on nickel (IMAC), and stored at −80° C.

CDK2/cyclineE Flashplate Test in 96-Well Format.

A format in streptavidin-coated 96-well plates is used to test the activity of the compounds on the kinase activity of CDK2/cycline E.

To perform this test, the biotinylated peptide substrate, a fragment of the protein pRb (biotinyl-SACPLNLPLQN-NHTAADMYLSPVRSPKKKGSTTROH), is dissolved at a concentration of 1 mM in kinase buffer (HEPES/NaOH 50 mM, NaCl 1 mM, MgCl$_2$ 5 mM, pH 7.5) in order to constitute a stock solution stored at −20° C. in the form of 110 µL aliquots. On the day of the experiment, an aliquot of this solution is thawed and diluted in kinase buffer containing 1 mM of dithiothreitol, added to the buffer extemporaneously, in order to obtain a concentration of 14.3 µM. 70 µL of this solution are added to each well of the Flashplate in order to obtain a final substrate concentration of 10 µM during the enzymatic reaction performed in a final volume of the reaction medium of 100 µL (cf. below).

Intermediate dilutions of inhibitors (products of the invention) at various concentrations are prepared in DMSO from stock solutions at 10 mM in separate tubes. Dilutions at 1000 µM, 333.3 µM, 111.1 µM, 37.03 µM, 12.35 µM, 4.11 µM and 1.37 µM are thus prepared. One µL of each of these solutions (or 1 µL of DMSO for the controls) is transferred into the wells of the test plate.

19 µl of a solution of a mixture of adenosine triphosphate (ATP) and of ATPγ$^{33}$P in kinase buffer at a total concentration of 5.26 µM of ATP and 52.6 µCi/ml of $^{33}$P are then added to each well. The enzymatic reaction is initiated by adding 10 µL per well of a 200 nM solution of CDK2/cycline E in kinase buffer containing 1 mM of dithiothreitol (or 10 µL of kinase buffer containing 1 mM of dithiothreitol for the reaction blanks).

After addition of each of the reagents, the final volume of each well is 100 µL, the final concentration of substrate is 10 µM, the final inhibitor concentrations are 10 µM, 3.33 µM, 1.11 µM, 0.37 µM, 0.123 µM, 0.041 µM and 0.014 µM (according to the concentration of the intermediate dilution), the final ATP concentration is 1 µM, the final amount of $^{33}$P is 1 µCi/well, and the final concentration of CDK2/cycline E complex is 20 nM.

After addition of all of the reagents, the test plate is incubated at 30° C. with orbital shaking at 650 rpm.

When the incubation is complete, the plate is washed three times with 300 µL per well of PBS (phosphate-buffered saline, pH=7.4, without calcium or magnesium, reference 10010-015, Gibco BRL). The incorporation of $^{33}$P to the peptide is quantified by scintillation counting with a Packard Topcount.NXT machine. The inhibitory activity of the products of the invention is evaluated by measuring the inhibitory concentration that allows a 50% reduction in the enzymatic activity (IC$_{50}$).

Results: Table 1:

| Example | IC 50 (nM) | | | | | |
|---|---|---|---|---|---|---|
| | FAK | KDR | TIE2 | Aurora A | Aurora B | CDK2 |
| 1 | 164 | 29 | 4 | 172 | 138 | |
| 2 | 299 | 150 | 21 | 222 | 196 | |
| 5 | 249 | 258 | 47 | 131 | 67 | |
| 7 | 184 | 34 | 9 | 553 | 133 | |

What is claimed is:

1. A compound of formula (I):

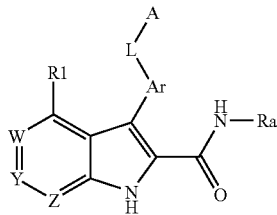

Formula (I)

wherein:
1) A and Ar are independently selected from the group consisting of: aryl, heteroaryl, substituted aryl, substituted heteroaryl, cycloalkyl, and substituted cycloalkyl;
2) L is selected from the group consisting of: bond, CO, NH, CO—NH, NH—CO, NH—SO, NH—SO$_2$, SO$_2$NH, NH—CH$_2$, CH$_2$—NH, CH$_2$—CO—NH, NH—CO—CH$_2$, NH—CH$_2$—CO, CO—CH$_2$—NH, NH—CO—NH, NH—CS—NH, and NH—CO—O, O—CO—NH;
3) one from among Y and Z is chosen from N and NO, and the other from among Y and Z is C(R5), and W is C(R6);
4) R1, R5, and R6 are each independently chosen from the group consisting of: H, halogen, R2, CN, O(R2), OC(O)(R2), OC(O)N(R2)(R3), OS(O$_2$)(R2), N(R2)(R3), N=C(R2)(R3), N(R2)C(O)(R3), N(R2)C(O)O(R3), N(R4)C(O)N(R2)(R3), N(R4)C(S)N(R2)(R3), N(R2)S(O$_2$)(R3), C(O)(R2), C(O)O(R2), C(O)N(R2)(R3), C(=N(R3))(R2), C(=N(OR3))(R2), S(R2), S(O)(R2), S(O$_2$)(R2), S(O$_2$)O(R2), and S(O$_2$)N(R2)(R3); in which each R2, R3, R4 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl, substituted heterocyclyl, alkylene, substituted alkylene, and substituted alkynyl; in which, when R2 and R3 are simultaneously present on one of the groups R1, R5 and R6, they may be linked together to form a ring;
5) Ra is selected from the group consisting of H, (C1-C4) alkyl and (C3-C4)cycloalkyl; or a pharmaceutically acceptable salt, hydrate or solvate of the compound of formula (I).

2. The compound according to claim 1, wherein Ra is H.
3. The compound according to claim 1, wherein R1, R5, and R6 are selected from H, halogen, OMe and methyl.
4. The compound according to claim 3, wherein R1, R5, and R6 are selected from H and F.
5. The compound according to claim 4, wherein R1, R5, and R6 are H.
6. The compound according to claim 5, wherein Y is selected from N and NO.
7. The compound according to claim 5, wherein Z is selected from N and NO.
8. The compound according to claim 1, wherein Ar is chosen from phenyl, pyridyl, thienyl, furyl and pyrrolyl, substituted with R11, in which R11 has the same definition as R5 as defined in claim 1.
9. The compound according to claim 8, wherein R11 is selected from the group consisting of H, F, Cl, methyl, NH$_2$, OCF$_3$ and CONH$_2$.

10. The compound according to claim 8, wherein Ar is an unsubstituted phenyl.
11. The compound according to claim 1, wherein L-A is chosen from NH—CO—NH-A and NH—SO$_2$-A.
12. The compound according to claim 1, wherein A is selected from the group consisting of phenyl, pyridyl, pyrimidyl, thienyl, furyl, pyrrolyl, oxazolyl, thiazolyl, isoxazolyl, isothiazolyl, pyrazolyl, imidazolyl, indolyl, indazolyl, benzimidazolyl, benzoxazolyl and benzothiazolyl; optionally substituted.
13. The compound according to claim 12, wherein A is chosen from phenyl, pyrazolyl and isoxazolyl; optionally substituted.
14. The compound according to claim 13, wherein A is phenyl.
15. The compound according to claim 12, in which A is substituted with a first substituent selected from the group consisting of alkyl, haloalkyl, alkylene, alkynyl, aryl, heteroaryl, O-alkyl, O-aryl, O-heteroaryl, S-alkyl, S-aryl and S-heteroaryl, each being optionally substituted with a substituent chosen from (C1-C3)alkyl, halogen and O—(C1-C3) alkyl.
16. The compound according to claim 15, in which A is substituted with a second substituent selected from the group consisting of F, Cl, Br, I, OH, SH, SO$_3$M, COOM, CN, NO$_2$, CON(R8)(R9), N(R8)CO(R9), (C1-C3)alkyl-OH, (C1-C3) alkyl-N(R8)(R9), (C1-C3)alkyl-(R10), (C1-C3)alkyl-COOH, and N(R8)(R9); in which R8 and R9 are independently chosen from H, (C1-C3)alkyl, (C1-C3)alkylOH, (C1-C3)haloalkyl, (C1-C3)alkylNH$_2$, (C1-C3)alkylCOOM, and (C1-C3)alkylSO$_3$M; in which, when R8 and R9 are simultaneously other than H, they may be linked to form a 5- to 7-membered ring comprising from 0 to 3 heteroatoms chosen from O, N and S; in which M is H or a cation of an alkali metal chosen from Li, Na and K; and in which R10 is H or an optionally substituted non-aromatic heterocycle containing 2 to 7 carbon atoms and 1 to 3 heteroatoms chosen from N, O and S.
17. The compound according to claim 11, wherein A is phenyl, pyrazolyl or isoxazolyl substituted with one or more halogen, (C1-C4)alkyl, (C1-C3)haloalkyl, O—(C1-C4) alkyl, S—(C1-C4)alkyl, O—(C1-C4)halo alkyl, or S—(C1-C4)halo alkyl, and in which, when A is disubstituted, the two substituents may be linked together to form a 5- to 7-membered ring containing from 0 to 3 heteroatoms chosen from N, O and S.
18. A compound according to claim 1 selected from the group consisting of:
   3-{4-[3-(2-fluoro-5-trifluoromethylphenyl)ureido]phenyl}-1H-pyrrolo[2,3-b]pyridine-2-carboxamide;
   3-{4-[3-(2-fluorophenyl)ureido]phenyl}-1H-pyrrolo[2,3-b]pyridine-2-carboxamide;
   3-{4-[3-(2-methoxyphenyl)ureido]phenyl}-1H-pyrrolo[2,3-b]pyridine-2-carboxamide;
   3-{4-[3-(4-trifluoromethylphenyl)ureido]phenyl}-1H-pyrrolo[2,3-b]pyridine-2-carboxamide;
   3-{4-[3-(2-chloro-5-trifluoromethylphenyl)ureido]phenyl}-1H-pyrrolo[2,3-b]pyridine-2-carboxamide;
   3-{4-[3-(2-fluoro-3-trifluoromethylphenyl)ureido]phenyl}-1H-pyrrolo[2,3-b]pyridine-2-carboxamide;
   3-{4-[3-(4-fluoro-3-trifluoromethylphenyl)ureido]phenyl}-1H-pyrrolo[2,3-b]pyridine-2-carboxamide;
   3-{4-[3-(3-fluoro-5-trifluoromethylphenyl)ureido]phenyl}-1H-pyrrolo[2,3-b]pyridine-2-carboxamide;
   3-{4-[3-(4-trifluoromethoxyphenyl)ureido]phenyl}-1H-pyrrolo[2,3-b]pyridine-2-carboxamide;

3-{4-[3-(3,4-dimethoxyphenyl)ureido]phenyl}-1H-pyrrolo[2,3-b]pyridine-2-carboxamide;
3-{4-[3-(2,5-dimethylphenyl)ureido]phenyl}-1H-pyrrolo[2,3-b]pyridine-2-carboxamide;
3-{4-[3-(3-methoxyphenyl)ureido]phenyl}-1H-pyrrolo[2,3-b]pyridine-2-carboxamide;
3-{4-[3-(3-trifluoromethylphenyl)ureido]phenyl}-1H-pyrrolo[2,3-b]pyridine-2-carboxamide;
3-{4-[3-(3,4-dimethylphenyl)ureido]phenyl}-1H-pyrrolo[2,3-b]pyridine-2-carboxamide;
3-{4-[3-(2-methoxy-5-methylphenyl)ureido]phenyl}-1H-pyrrolo[2,3-b]pyridine-2-carboxamide;
3-[4-(3-m-tolylureido)phenyl]-1H-pyrrolo[2,3-b]pyridine-2-carboxamide;
3-{4-[3-(4-fluorophenyl)ureido]phenyl}-1H-pyrrolo[2,3-b]pyridine-2-carboxamide;
3-[4-(3-p-tolylureido)phenyl]-1H-pyrrolo[2,3-b]pyridine-2-carboxamide;
3-{4-[3-(4-methyl-3-trifluoromethylphenyl)ureido]phenyl}-1H-pyrrolo[2,3-b]pyridine-2-carboxamide;
3-{4-[3-(4-difluoromethoxyphenyl)ureido]phenyl}-1H-pyrrolo[2,3-b]pyridine-2-carboxamide;
3-{4-[3-(3,5-dimethoxyphenyl)ureido]phenyl}-1H-pyrrolo[2,3-b]pyridine-2-carboxamide;
3-{4-[3-(4-chloro-3-trifluoromethylphenyl)ureido]phenyl}-1H-pyrrolo[2,3-b]pyridine-2-carboxamide;
3-{4-[3-(2,5-dimethoxyphenyl)ureido]phenyl}-1H-pyrrolo[2,3-b]pyridine-2-carboxamide;
3-{4-[3-(3-fluorophenyl)ureido]phenyl}-1H-pyrrolo[2,3-b]pyridine-2-carboxamide;
3-{4-[3-(2-methoxy-5-trifluoromethylphenyl)ureido]phenyl}-1H-pyrrolo[2,3-b]pyridine-2-carboxamide; and
3-{4-[3-(3-ethylphenyl)ureido]phenyl}-1H-pyrrolo[2,3-b]pyridine-2-carboxamide;
or a pharmaceutically acceptable salt thereof.

19. A compound according to claim 1, characterized in that it is:
3-{4-[3-(2-fluoro-5-trifluoromethylphenyl)ureido]phenyl}-7-oxy-1H-pyrrolo[2,3-b]pyridine-2-carboxamide, or a pharmaceutically acceptable salt thereof.

20. A compound according to claim 1 selected from the group consisting of:
3-{4-[3-(2-fluoro-5-trifluoromethylphenyl)ureido]phenyl}-1H-pyrrolo[2,3-c]pyridine-2-carboxamide;
3-{4-[3-(2-methoxy-5-methylphenyl)ureido]phenyl}-1H-pyrrolo[2,3-c]pyridine-2-carboxamide;
3-{4-[3-(3-chlorophenyl)ureido]phenyl}-1H-pyrrolo[2,3-c]pyridine-2-carboxamide trifluoroacetate;
3-{4-[3-(3-chloro-4-fluorophenyl)ureido]phenyl}-1H-pyrrolo[2,3-c]pyridine-2-carboxamide trifluoroacetate;
3-{4-[3-(2-fluoro-5-methylphenyl)ureido]phenyl}-1H-pyrrolo[2,3-c]pyridine-2-carboxamide trifluoroacetate;
3-[4-(3-m-tolylureido)phenyl]-1H-pyrrolo[2,3-c]pyridine-2-carboxamide trifluoroacetate;
3-{4-[3-(2-acetylamino-5-trifluoromethylphenyl)ureido]phenyl}-1H-pyrrolo[2,3-c]pyridine-2-carboxamide trifluoroacetate;
3-{4-[3-(2-methoxyphenyl)ureido]phenyl}-1H-pyrrolo[2,3-c]pyridine-2-carboxamide;
3-{4-[3-(2-trifluoromethylphenyl)ureido]phenyl}-1H-pyrrolo[2,3-c]pyridine-2-carboxamide;
3-{4-[3-(3-trifluoromethylphenyl)ureido]phenyl}-1H-pyrrolo[2,3-c]pyridine-2-carboxamide;
3-{4-[3-(4-fluorophenyl)ureido]phenyl}-1H-pyrrolo[2,3-c]pyridine-2-carboxamide;
3-{4-[3-(4-trifluoromethylphenyl)ureido]phenyl}-1H-pyrrolo[2,3-c]pyridine-2-carboxamide;
3-[4-(3-p-tolylureido)phenyl]-1H-pyrrolo[2,3-c]pyridine-2-carboxamide;
3-{4-[3-(4-chloro-3-trifluoromethylphenyl)ureido]phenyl}-1H-pyrrolo[2,3-c]pyridine-2-carboxamide;
3-{4-[3-(2-chloro-5-trifluoromethylphenyl)ureido]phenyl}-1H-pyrrolo[2,3-c]pyridine-2-carboxamide;
3-{4-[3-(4-trifluoromethoxyphenyl)ureido]phenyl}-1H-pyrrolo[2,3-c]pyridine-2-carboxamide;
3-{4-[3-(4-difluoromethoxyphenyl)ureido]phenyl}-1H-pyrrolo[2,3-c]pyridine-2-carboxamide;
3-{4-[3-(3,4-dimethylphenyl)ureido]phenyl}-1H-pyrrolo[2,3-c]pyridine-2-carboxamide;
3-{4-[3-(3,5-dimethoxyphenyl)ureido]phenyl}-1H-pyrrolo[2,3-c]pyridine-2-carboxamide;
3-{4-[3-(2,5-dimethylphenyl)ureido]phenyl}-1H-pyrrolo[2,3-c]pyridine-2-carboxamide;
3-{4-[3-(2-fluorophenyl)ureido]phenyl}-1H-pyrrolo[2,3-c]pyridine-2-carboxamide;
3-{4-[3-(3-fluorophenyl)ureido]phenyl}-1H-pyrrolo[2,3-c]pyridine-2-carboxamide;
3-{4-[3-(2-fluoro-3-trifluoromethylphenyl)ureido]phenyl}-1H-pyrrolo[2,3-c]pyridine-2-carboxamide;
3-{4-[3-(3-fluoro-5-trifluoromethylphenyl)ureido]phenyl}-1H-pyrrolo[2,3-c]pyridine-2-carboxamide;
3-{4-[3-(4-fluoro-3-trifluoromethylphenyl)ureido]phenyl}-1H-pyrrolo[2,3-c]pyridine-2-carboxamide;
3-{4-[3-(4-methyl-3-trifluoromethylphenyl)ureido]phenyl}-1H-pyrrolo[2,3-c]pyridine-2-carboxamide;
3-{4-[3-(3-methoxyphenyl)ureido]phenyl}-1H-pyrrolo[2,3-c]pyridine-2-carboxamide trifluoroacetate;
3-{4-[3-(3,4-dimethoxyphenyl)ureido]phenyl}-1H-pyrrolo[2,3-c]pyridine-2-carboxamide trifluoroacetate;
3-{4-[3-(2,5-dimethoxyphenyl)ureido]phenyl}-1H-pyrrolo[2,3-c]pyridine-2-carboxamide trifluoroacetate;
3-[4-(3-o-tolylureido)phenyl]-1H-pyrrolo[2,3-c]pyridine-2-carboxamide,
3-{4-[3-(4-methoxyphenyl)ureido]phenyl}-1H-pyrrolo[2,3-c]pyridine-2-carboxamide;
3-{4-[3-(3-chloro-4-difluoromethoxyphenyl)ureido]phenyl}-1H-pyrrolo[2,3-c]pyridine-2-carboxamide;
3-{4-[3-(3,5-dimethylphenyl)ureido]phenyl}-1H-pyrrolo[2,3-c]pyridine-2-carboxamide; and
3-{4-[3-(3-ethylphenyl)ureido]phenyl}-1H-pyrrolo[2,3-c]pyridine-2-carboxamide;
or a pharmaceutically acceptable salt thereof.

21. The compound according to claim 1, in combination with a pharmaceutically acceptable excipient.

22. A method for inhibiting a reaction catalysed by a kinase selected from FAK, KDR, Tie2, Aurora A, Aurora B and CDK2, the method comprising contacting said kinase with an effective amount of a compound according to claim 1.

23. A process for preparing a compound of formula (I) as defined in claim 1, wherein a compound of formula (V):

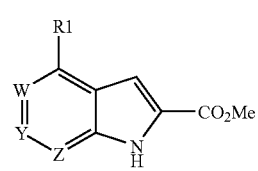

(V)

wherein R1, W, Y, and Z are as defined for the compound of formula (I) in claim 1; is subjected to the following steps:

a) halogenation in position 3, followed by
b) Suzuki coupling in position 3, to obtain a compound of formula (III) below:

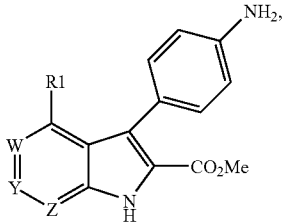
(III)

followed by c) amidation of the ester in position 2 to obtain the compound of formula (II) below:

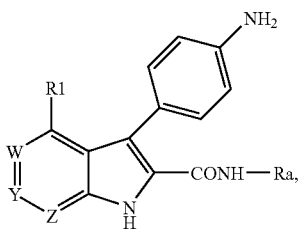
(II)

followed by d) acylation of the aminophenyl group in position 3.

24. A compound of formula (II):

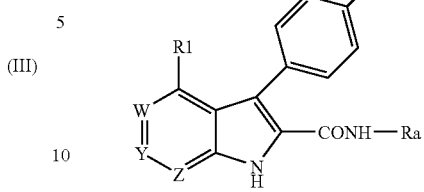
(II)

wherein:

one from among Y and Z is chosen from N and NO, and the other from among Y and Z is C(R5);

W is C(R6);

R1, R5, and R6 are each independently chosen from the group consisting of: H, halogen, R2, CN, 0(R2), OC(O)(R2), OC(O)N(R2)(R3), OS(O$_2$)(R2), N(R2)(R3), N=C(R2)(R3), N(R2)C(O)(R3), N(R2)C(O)O(R3), N(R4)C(O)N(R2)(R3), N(R4)C(S)N(R2)(R3), N(R2)S(O$_2$)(R3), C(O)(R2), C(O)O(R2), C(O)N(R2)(R3), C(=N(R3))(R2), C(=N(OR3))(R2), S(R2), S(O)(R2), S(O$_2$)(R2), S(O$_2$)O(R2), and S(O$_2$)N(R2)(R3); in which each R2, R3, R4 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl, substituted heterocyclyl, alkylene, substituted alkylene, and substituted alkynyl; in which, when R2 and R3 are simultaneously present on one of the groups R1, R5 and R6, they may be linked together to form a ring; and Ra is selected from the group consisting of H, (C1-C4) alkyl and (C3-C4)cycloalkyl.

* * * * *

UNITED STATES PATENT AND TRADEMARK OFFICE
CERTIFICATE OF CORRECTION

| | | |
|---|---|---|
| PATENT NO. | : 7,947,706 B2 | Page 1 of 1 |
| APPLICATION NO. | : 11/870640 | |
| DATED | : May 24, 2011 | |
| INVENTOR(S) | : Michel Tabart et al. | |

It is certified that error appears in the above-identified patent and that said Letters Patent is hereby corrected as shown below:

Title Page, Item (73) should read

(73) Assignee: AVENTIS PHARMA S.A., Antony (FR)

Signed and Sealed this
Thirteenth Day of March, 2012

David J. Kappos
*Director of the United States Patent and Trademark Office*